United States Patent
Zhang et al.

(10) Patent No.: US 9,709,886 B2
(45) Date of Patent: Jul. 18, 2017

(54) SULFONIC ACID DERIVATIVE COMPOUNDS AS PHOTOACID GENERATORS IN RESIST APPLICATIONS

(71) Applicant: Heraeus Precious Metals North America Daychem LLC, Vandalia, OH (US)

(72) Inventors: Yongqiang Zhang, Centerville, OH (US); Daniel Greene, Dayton, OH (US); Ram B. Sharma, Centerville, OH (US)

(73) Assignee: HERAEUS PRECIOUS METALS NORTH AMERICA DAYCHEM LLC, Vandalia, OH (US)

( * ) Notice: Subject to any disclaimer, the term of this patent is extended or adjusted under 35 U.S.C. 154(b) by 0 days.

(21) Appl. No.: 15/264,966

(22) Filed: Sep. 14, 2016

(65) Prior Publication Data

US 2017/0003587 A1    Jan. 5, 2017

Related U.S. Application Data

(63) Continuation of application No. 14/657,387, filed on Mar. 13, 2015, now Pat. No. 9,477,150.

(51) Int. Cl.
    C07D 221/14    (2006.01)
    G03F 7/038     (2006.01)
    (Continued)

(52) U.S. Cl.
    CPC ......... *G03F 7/0045* (2013.01); *C07D 221/14* (2013.01); *C08K 5/42* (2013.01); *G03F 7/025* (2013.01); *G03F 7/027* (2013.01); *G03F 7/039* (2013.01); *G03F 7/16* (2013.01); *G03F 7/162* (2013.01); *G03F 7/20* (2013.01);
    (Continued)

(58) Field of Classification Search
    None
    See application file for complete search history.

(56) References Cited

U.S. PATENT DOCUMENTS

| 5,076,831 A | 12/1991 | Saupe et al. |
| 5,128,232 A | 7/1992  | Thackeray et al. |

(Continued)

FOREIGN PATENT DOCUMENTS

| CA | 2169713 A1 | 8/1996 |
| CN | 1616429 A  | 5/2005 |

(Continued)

OTHER PUBLICATIONS

Birch et al., "The Synthesis of (±) -Xanthorrhoein" J. Chem. Soc. Section C, Jan. 1, 1966, pp. 523-527.

(Continued)

*Primary Examiner* — Martin Angebranndt
(74) *Attorney, Agent, or Firm* — Stradley Ronon Stevens & Young, LLP

(57) ABSTRACT

Novel photoacid generator compounds are provided. Photoresist compositions that include the novel photoacid generator compounds are also provided. The invention further provides methods of making and using the photoacid generator compounds and photoresist compositions disclosed herein. The compounds and compositions are useful as photoactive components in chemically amplified resist compositions for various microfabrication applications.

21 Claims, 4 Drawing Sheets

(51) Int. Cl.
G03F 7/039 (2006.01)
G03F 7/38 (2006.01)
G03F 7/30 (2006.01)
G03F 7/20 (2006.01)
G03F 7/004 (2006.01)
G03F 7/027 (2006.01)
C08K 5/42 (2006.01)
G03F 7/025 (2006.01)
G03F 7/16 (2006.01)
G03F 7/32 (2006.01)

(52) U.S. Cl.
CPC ............... *G03F 7/30* (2013.01); *G03F 7/322* (2013.01); *G03F 7/38* (2013.01)

(56) References Cited

U.S. PATENT DOCUMENTS

| | | | |
|---|---|---|---|
| 6,114,463 | A | 9/2000 | Chen et al. |
| 7,479,361 | B2 | 1/2009 | Nagahara et al. |
| 7,534,554 | B2 | 5/2009 | Nagahara et al. |
| 7,592,126 | B2 | 9/2009 | Nishiyama |
| 7,608,715 | B2 | 10/2009 | Naik et al. |
| 7,947,839 | B2 | 5/2011 | Gazzard et al. |
| 8,183,310 | B2 | 5/2012 | Naik et al. |
| 8,188,112 | B2 | 5/2012 | Uttam et al. |
| 8,268,531 | B2 | 9/2012 | Ober et al. |
| 8,329,377 | B2 | 12/2012 | Takemoto et al. |
| 8,329,413 | B2 | 12/2012 | Wong et al. |
| 8,362,276 | B2 | 1/2013 | Chung et al. |
| 8,455,176 | B2 | 6/2013 | Houlihan et al. |
| 8,609,891 | B2 | 12/2013 | Bae et al. |
| 8,680,268 | B2 | 3/2014 | Murai et al. |
| 8,748,894 | B2 | 6/2014 | Kim et al. |
| 9,383,644 | B2 | 7/2016 | Zhang et al. |
| 9,477,150 | B2 * | 10/2016 | Zhang ............... G03F 7/027 |
| 2002/0045130 | A1 | 4/2002 | Nitta et al. |
| 2003/0082481 | A1 | 5/2003 | Lee et al. |
| 2005/0244364 | A1 | 11/2005 | Luukas et al. |
| 2005/0271616 | A1 | 12/2005 | Luukas et al. |
| 2006/0210922 | A1 * | 9/2006 | Nishiyama ........... G03F 7/0045 430/270.1 |
| 2007/0037785 | A1 | 2/2007 | Ansorge et al. |
| 2008/0226581 | A1 | 9/2008 | Luukas |
| 2009/0305429 | A1 | 12/2009 | Eichen et al. |
| 2011/0008635 | A1 | 1/2011 | Kliesch et al. |
| 2011/0129777 | A1 | 6/2011 | Hatakeyama et al. |
| 2011/0223535 | A1 | 9/2011 | Liu et al. |
| 2011/0229821 | A1 * | 9/2011 | Dautel ................ B41M 5/0023 430/270.1 |
| 2012/0077120 | A1 | 3/2012 | Prokopowicz et al. |
| 2012/0183984 | A1 | 7/2012 | He et al. |
| 2012/0289697 | A1 * | 11/2012 | Murai ................. C07D 221/14 544/126 |
| 2014/0038102 | A1 * | 2/2014 | Park ..................... G03F 7/038 430/270.1 |
| 2015/0299132 | A1 * | 10/2015 | Hirahara ............. C07D 221/14 546/98 |
| 2016/0085148 | A1 * | 3/2016 | Zhang ................... G03F 7/027 430/286.1 |

FOREIGN PATENT DOCUMENTS

| | | |
|---|---|---|
| CN | 103073538 A | 5/2013 |
| DE | 19820947 A1 | 11/1998 |
| DE | 19821263 A1 | 11/1998 |
| DE | 19726241 A1 | 12/1998 |
| EP | 0164248 A2 | 12/1985 |
| EP | 1586570 A1 | 10/2005 |
| EP | 1663223 B1 | 6/2006 |
| EP | 2163949 A1 | 3/2010 |
| EP | 3018182 * | 5/2016 |
| JP | 2002-251011 | 9/2002 |
| JP | 2004-217748 A | 8/2004 |
| JP | 2004-243676 A | 9/2004 |
| JP | 2006-299091 | 11/2006 |
| JP | 2014-094926 * | 5/2014 |
| JP | 2014-160199 * | 9/2014 |
| KR | 10-2014-0103839 A | 8/2014 |
| TW | 201437765 A | 10/2014 |
| WO | 98/51772 A1 | 11/1998 |
| WO | 2012/112232 A1 | 8/2012 |
| WO | 2012/113720 A2 | 8/2012 |
| WO | 2012/113722 A2 | 8/2012 |
| WO | 2012/113723 A2 | 8/2012 |
| WO | 2012/113724 A2 | 8/2012 |
| WO | 2012/113725 A2 | 8/2012 |
| WO | 2012/120141 A1 | 9/2012 |
| WO | 2012/135416 A1 | 10/2012 |
| WO | 2013/040020 A1 | 3/2013 |
| WO | 2014/061063 | 4/2014 |
| WO | 2014/073409 A1 | 5/2014 |
| WO | 2014/084269 A1 | 6/2014 |
| WO | 2015/001804 * | 1/2015 |
| WO | WO2015/046501 | 4/2015 |

OTHER PUBLICATIONS

Ikeda, Takuya et al: "Naphthalimide sulfonate ester-type nonionic photoacid generators, and resin compositions for photolithography" WO 2015/001804 A1 San-Apro Ltd., Japan, Jan. 8, 2015, Database CA [Online] Chemical Abstracts Service, Columbus, Ohio, US; XP002748895, retrieved from STN Database accession No. 2015:35766 Abstract; CAS-RNs 1643931-90-1, 1643931-92-3, 1643931-93-4, 1643932-01-7, 1643932-17-5, 1643932-18-6, 1643932-23-3, 1643932-36-8, 1643932-37-9, 1643932-38-0, 1643932-43-7 (24 pages).

International Search Report and Written Opinion for international patent application No. PCT/US2015/047089 mailed Feb. 19, 2016 by the European Patent Office in its capacity as International Searching Authority.

International Search Report and Written Opinion mailed Apr. 8, 2016 for counterpart international patent application No. PCT/US2016/017573.

Kodama et al., "Synthesis and Properties of Novel i- and g-Line Sensitive Photoacid Generators Based on 9-Fluorenone Derivatives with Aryl-Ethynyl Units" Chem. Lett. 2012, 41, pp. 625-627 Published on the web May 26, 2012.

Machine English translation of JP 2004-217748; JP 2004-217748 published Aug. 5, 2004—Applicant: Konica Minolta Holdings Inc.

Partial Machine English translation of WO 2015/001804; WO 2015/001804 published Jan. 8, 2015—Applicant: San-Apro Ltd.

Plakidin et al., "Naphthalic acid derivatives. VI. Reaction of 4-bromo- and 4-methoxy-N-acyloxynaphthaloimides with alkaline solutions" Zhurnal Organicheskoi Khimii vol. 9, No. 1, 1973, pp. 171-175—Abstract Only—Database CA [Online] Chemical Abstracts Service, Columbus, Ohio, US, XP002748893, retrieved from STN Database accession No. 1973:147636 Abstract; CAS-RN 40812-75-7 (one page).

Sakita, Kyouhei: "Photosensitive polymer compositions containing naphthalimidyl sulfonate acid generators, their cured films, their manufacture, and liquid crystal displays and organic electroluminescent (EL) displays using them" Apr. 2, 2015, Database CA [Online] Chemical Abstracts Service, Columbus, Ohio, US; XP002749075, retrieved from STN Database accession No. 2015:565519 (10 pages).

Office Action and Search Report dated Apr. 8, 2016 for related Taiwan application No. 104128517 with English translation of Search Report attached.

* cited by examiner

SULFONIC ACID DERIVATIVE COMPOUNDS AS PHOTOACID GENERATORS IN RESIST APPLICATIONS

CROSS-REFERENCE TO RELATED APPLICATIONS

This patent application is a continuation application of U.S. Ser. No. 14/657,387, filed on Mar. 13, 2015, the disclosure of which is incorporated herein by reference in its entirety.

TECHNICAL FIELD

The invention relates to new photoacid generator compounds ("PAGs") and photoresist compositions that comprise such PAG compounds. In particular, the PAG compounds of the invention have excellent solubility in organic solvents and exhibit higher sensitivity and better performance in a photolithographic process than conventional PAG compounds.

BACKGROUND

Photoresists are photosensitive films for transfer of images to a substrate. They form negative or positive images. After coating a photoresist on a substrate, the coating is exposed through a patterned photomask to a source of activating energy, such as ultraviolet light, to form a latent image in the photoresist coating. The photomask has areas opaque and transparent to activating radiation that define an image desired to be transferred to the underlying substrate.

Chemical amplification-type photoresists have proven to be useful in achieving high sensitivity in processes for forming ultrafine patterns in the manufacture of semiconductors. These photoresists are prepared by blending a PAG with a polymer matrix having acid labile structures. According to the reaction mechanism of such a photoresist, the photoacid generator generates acid when it is irradiated by the light source, and the main chain or branched chain of the polymer matrix in the exposed or irradiated portion reacts in a so called "post exposure bake" (PEB) with the generated acid and is decomposed or cross-linked, so that the polarity of the polymer is altered. This alteration of polarity results in a solubility difference in the developing solution between the irradiated exposed area and the unexposed area, thereby forming a positive or negative image of a mask on the substrate. Acid diffusion is important not only to increase photoresist sensitivity and throughput, but also to limit line edge roughness due to shot noise statistics.

In a chemically amplified photoresist, the solubility-switching chemistry necessary for imaging is not caused directly by the exposure; rather exposure generates a stable catalytic species that promotes solubility-switching chemical reactions during the subsequent PEB step. The term "chemical amplification" arises from the fact that each photochemically-generated catalyst molecule can promote many solubility-switching reaction events. The apparent quantum efficiency of the switching reaction is the quantum efficiency of catalyst generation multiplied by the average catalytic chain length. The original exposure dose is "amplified" by the subsequent chain of chemical reaction events. The catalytic chain length for a catalyst can be very long (up to several hundred reaction events) giving dramatic exposure amplification.

Chemical amplification is advantageous in that it can greatly improve resist sensitivity, but it is not without potential drawbacks. For instance as a catalyst molecule moves around to the several hundred reactions sites, nothing necessarily limits it to the region that was exposed to the imaging radiation. There is a potential trade-off between resist sensitivity and imaging fidelity. For example, the amplified photoresist is exposed through a photomask, generating acid catalyst in the exposed regions. The latent acid image generated in the first step is converted into an image of soluble and insoluble regions by raising the temperature of the wafer in the PEB, which allows chemical reactions to occur. Some acid migrates out of the originally exposed region causing "critical dimension bias" problems. After baking, the image is developed with a solvent. The developed feature width may be larger than the nominal mask dimension as the result of acid diffusion from exposed into the unexposed regions. For much of the history of amplified resists this trade-off was of little concern as the catalyst diffusion distances were insignificant relative to the printed feature size, but as feature sizes have decreased, the diffusion distances have remained roughly the same and catalyst diffusion has emerged as a significant concern.

In order to generate enough acid which would change the solubility of the polymer, a certain exposure time is required. For a known PAG molecule like N-Hydroxynaphthalimide triflate ("NIT"), this exposure time is rather long (due to its low absorption at 365 nm or longer). Increasing the concentration of such PAGs, however, will not result in faster exposure times because the solubility of the PAG is the limiting factor. Another possibility is to add sensitizers which absorb the light and transfer energy to the PAG which would then liberate the acid. Such sensitizers, however, must be used in rather high concentrations in order to be able to transfer the energy to a PAG in close proximity. At such high concentrations, sensitizers often have an absorption which is too high and has negative effects on the shape of the resist profile after development.

Accordingly, there is a need in the art for PAGs that exhibit better a solubility, which means that more active molecules are imparted into the formulation, wherein a photoresist composition comprising these compounds has a high sensitivity towards electromagnetic radiation, in particular towards electromagnetic radiation with a wavelength of 200 to 500 nm, and—at the same time—allows the production of a patterned structure with a higher resolution, compared to the photoresist compositions known from the prior art.

SUMMARY

The invention satisfies this need by providing sulfonic acid derivative compound represented by either Formula (I) or Formula (II):

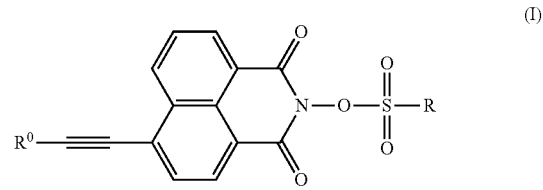

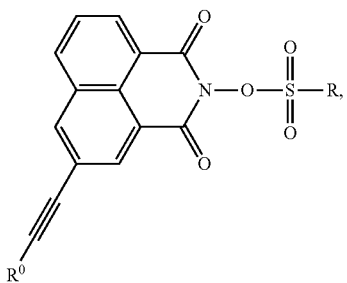

(II)

wherein R ad R⁰ are as defined herein.

In some embodiments, the invention also provides resist compositions comprising imaging-effective amounts of one or more PAG according to the invention and a resin.

In other embodiments, the invention provides methods for forming relief images of the photoresists of the invention, including methods for forming highly resolved patterned photoresist images (e.g., a patterned line having essentially vertical sidewalls) of sub-quarter micron dimensions or less, such as sub-0.2 or sub-0.1 micron dimensions.

The invention further provides articles of manufacture comprising substrates such as a microelectronic wafer or a flat panel display substrate having coated thereon the photoresists and relief images of the invention. Other aspects of the invention are disclosed infra.

BRIEF DESCRIPTION OF DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION

Definitions

Figure 1:
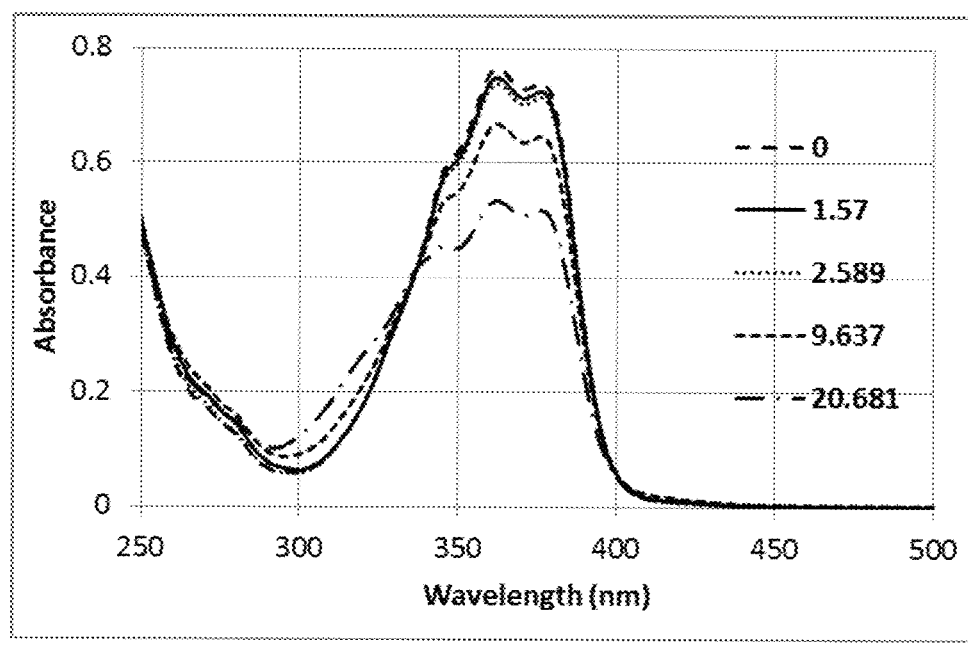
FIG. 1 is a UV-Vis spectra of compound T3 upon irradiating with a UV lamp at 365 nm, showing the decrease of the intensity with the increase of exposure dose of energy (mJ/cm²)

Unless otherwise stated, the following terms used in this Application, including the specification and claims, have the definitions given below. It must be noted that, as used in the specification and the appended claims, the singular forms "a," "an," and "the" include plural referents unless the context clearly dictates otherwise.

All numerical designations, such as, weight, pH, temperature, time, concentration, and molecular weight, including ranges, are approximations which are varied by 10%. It is to be understood, although not always explicitly stated, that all numerical designations are preceded by the term "about." It also is to be understood, although not always explicitly stated, that the reagents described herein are merely exemplary and that equivalents of such are known in the art.

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, the term "moiety" refers to a specific segment or functional group of a molecule. Chemical moieties are often recognized chemical entities embedded in or appended to a molecule.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing from 1-20 (e.g., 2-18, 3-18, 1-8, 1-6, 1-4, or 1-3) carbon atoms. An alkyl group can be straight, branched, cyclic or any combination thereof. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents or can be multicyclic as set forth below.

Unless specifically limited otherwise, the term "alkyl," as well as derivative terms such as "alkoxy" and "thioalkyl," as used herein, include within their scope, straight chain, branched chain and cyclic moieties.

As used herein, an "alkenyl" group refers to an aliphatic carbon group that contains from 2-20 (e.g., 2-18, 2-8, 2-6, or 2-4) carbon atoms and at least one double bond. Like an alkyl group, an alkenyl group can be straight, branched or cyclic or any combination thereof. Examples of an alkenyl group include, but are not limited to, allyl, isoprenyl, 2-butenyl, and 2-hexenyl. An alkenyl group can be optionally substituted with one or more substituents as set forth below.

As used herein, an "alkynyl" group refers to an aliphatic carbon group that contains from 2-20 (e.g., 2-8, 2-6, or 2-4) carbon atoms and has at least one triple bond. An alkynyl group can be straight, branched or cyclic or any combination thereof. Examples of an alkynyl group include, but are not limited to, propargyl and butynyl. An alkynyl group can be optionally substituted with one or more substituents as set forth below.

A "halogen" is an atom of the 17th Group of the period table, which includes fluorine, chlorine, bromine and iodine.

As used herein, an "aryl" group used alone or as part of a larger moiety as in "aralkyl," "aralkoxy," or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents as set forth below.

As used herein, an "aralkyl" or "arylalkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, azacycloalkyl, or ((aminocarbonyl)cycloalkyl)cycloalkyl.

As used herein, the term "heteroaryl" group refers to a monocyclic, bicyclic, or tricyclic ring system having 4 to 18 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents as is set forth below.

A "heteroarylalkyl" group, as used herein, refers to an alkyl group (e.g., a $C_{1-4}$ alkyl group) that is substituted with a heteroaryl group. Both "alkyl" and "heteroaryl" have been defined above. A heteroarylalkyl is optionally substituted with one or more substituents as is set forth below.

As used herein, an "acyl" group refers to a formyl group or $R^X$—C(O)— (such as -alkyl-C(O)—, also referred to as "alkylcarbonyl") where "alkyl" have been defined previously.

As used herein, the term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups.

As used herein, an "alkoxy" group refers to an alkyl-O— group where "alkyl" has been defined previously.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, "Alkoxycarbonyl" means —COOR where R is alkyl as defined above, e.g., methoxycarbonyl, ethoxycarbonyl, and the like.

As used herein, a "sulfonyl" group refers to —S(O)$_2$—R$^x$ when used terminally and —S(O)$_2$— when used internally.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$alkylthio, and heteroatom-substituted $C_n$alkylthio. In certain embodiments, lower alkylthios are contemplated.

As used herein, the term "amine" or "amino" includes compounds where a nitrogen atom is covalently bonded to at least one carbon or heteroatom. The term "amine" or "amino" also includes —NH$_2$ and also includes substituted moieties. The term includes "alkyl amino" which comprises groups and compounds wherein the nitrogen is bound to at least one additional alkyl group. The term includes "dialkyl amino" groups wherein the nitrogen atom is bound to at least two additional independently selected alkyl groups. The term includes "arylamino" and "diarylamino" groups wherein the nitrogen is bound to at least one or two independently selected aryl groups, respectively.

The term "haloalkyl" refers to alkyl groups substituted with from one up to the maximum possible number of halogen atoms. The terms "haloalkoxy" and "halothioalkyl" refer to alkoxy and thioalkyl groups substituted with from one up to five halogen atoms.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein any of the above moieties or those introduced below can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

Modifications or derivatives of the compounds disclosed throughout this specification are contemplated as being useful with the methods and compositions of the invention. Derivatives may be prepared and the properties of such derivatives may be assayed for their desired properties by any method known to those of skill in the art. In certain aspects, "derivative" refers to a chemically modified compound that still retains the desired effects of the compound prior to the chemical modification.

Sulfonic Acid Derivate Photoacid Generator Compounds

The sulfonic acid derivative compounds according to the invention can be used as photoacid generators as will be explained in more detail below. Surprisingly, it has been discovered that PAG compounds of the invention are characterized by excellent solubility and photoreactivity towards electromagnetic radiation, in particular towards electromagnetic radiation with a wavelength in the range from 150 to 500 nm, preferably in the range from 300 to 450 nm, more preferably in the range from 350 to 440 nm, more preferably at wavelengths of 365 nm (i-line), 405 (h-line) and 436 nm (g-line).

The sulfonic acid derivative compounds according to the invention are N-hydroxynaphthalimide sulfonate derivatives represented by either Formula (I) or Formula (II):

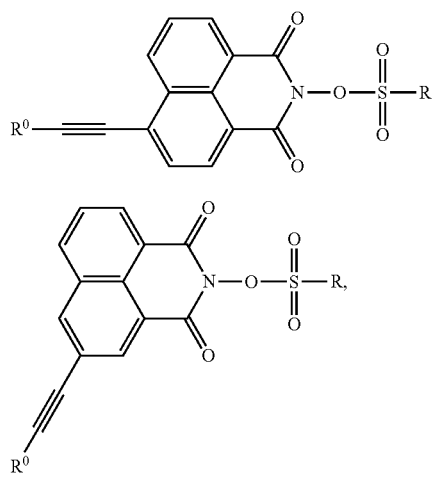

wherein $R^0$ is selected from the group consisting of
an aliphatic group having a carbon number of from 1 to 18 in which one or more hydrogen atoms may be substituted by a halogen atom,
an aliphatic group having a carbon number of from 2 to 18 which comprises at least one moiety selected from the group consisting of —O—, —S—, —C(=O)—, —C(=O)—O—, —C(=O)—S—, —O—C(=O)—O—, —C(=O)—NH—, —O—C(=O)—NH—, —C(=O)—NR$_a$—, —O—C(=O)—NR—, and —C(=O)—NR$_a$R$_b$, wherein R$_a$ and R$_b$ are each independently an aliphatic group with a carbon number of from 1 to 10, which may be the same or different and may be connected to form an alicyclic group, and wherein the aliphatic group optionally comprises at least one halogen atom; and
R is selected from the group consisting of
—CH$_3$, —CH$_2$F, —CHF$_2$, or —CF$_3$,
an aliphatic group having a carbon number of from 2 to 18, which may be substituted by one or more halogen atom(s),
an aliphatic group having a carbon number of from 2 to 18 which comprises at least one moiety selected from the group consisting of —O—, —S—, —C(=O)—, —C(=O)—O—, —C(=O)—S—, —O—C(=O)—O—, —C(=O)—NH—, —O—C(=O)—NH—, —C(=O)—NR$_a$—, —O—C(=O)—NR$_a$—, and —C(=O)—NR$_a$R$_b$, wherein R$_a$ and R$_b$ are as defined above, wherein the aliphatic group optionally comprises at least one halogen atom,
an aryl or heteroaryl group having a carbon number of from 4 to 18 in which one or more hydrogen atoms may be substituted by a halogen atom, an aliphatic, an haloalkyl, an alkoxy, a haloalkoxy, an alkylthio, a bisalkylamino, an acyloxy, an acylthio, an acylamino, an alkoxycarbonyl, an alkylsulfonyl, an alkylsulfinyl, an alicyclic, a heterocyclic, an aryl, an alkylaryl, a cyano, or a nitro group, and
an arylalkyl or heteroarylalkyl group having a carbon number of from 4 to 18 in which one or more hydrogen atoms in the aryl or heteroaryl group may be substituted by a halogen atom, an aliphatic, a haloalkyl, an alkoxy, a haloalkoxy, an alkylthio, a bisalkylamino, an acyloxy, an acylthio, an acylamino, an alkoxycarbonyl, an alkylsulfonyl, an alkylsulfinyl, an alicyclic, a heterocyclic, an aryl, an alkylaryl, a cyano, or a nitro group,
with the proviso that, if R is —CF$_3$, then $R^0$ is selected from the group consisting of
a hydrogen atom;
an aliphatic group having a carbon number of from 2 to 18 which comprises at least one moiety selected from the group consisting of —O—, —S—, —C(=O)—, —C(=O)—O—, —C(=O)—S—, —O—C(=O)—O—, —C(=O)—NH—, —O—C(=O)—NH—, —C(=O)—NR$_a$—, —O—C(=O)—NR$_a$—, and —C(=O)—NR$_a$R$_b$, wherein R$_a$ and R$_b$ are as defined above, wherein the aliphatic group optionally comprises at least one halogen atom;
—CH$_2$CH(CH$_3$)$_2$, —CH$_2$CH=CHCH$_3$, or —CH$_2$CH$_2$CH=CH$_2$,
a group represented by the Formula (A):
—CH$_2$—R$^{11}$ (A), wherein R$^{11}$ is selected from the group consisting of an aliphatic group having a carbon number of from 4 to 18,
cyclopropenyl, and
a group represented by the Formula (B):

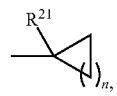

wherein R$^{21}$ is selected from the group consisting of a hydrogen atom or an alkyl group having a carbon number of from 1 to 10; and n is equal to 1 to 5.

In some embodiments, $R^0$ in Formulas (I) and (II) is an aliphatic group having a carbon number of from 1 to 18 in which one or more hydrogen atoms may be substituted by a halogen atom. Preferred examples include methyl, ethyl, propyl, isopropyl, butyl, isobutyl, sec-butyl, tert-butyl, n-pentyl, n-hexyl, 2-ethylhexyl, n-heptyl, n-octyl, n-nonyl, and n-decyl. In an embodiment, $R^0$ in Formulas (I) and (II) is an aliphatic group having a carbon number of from 1 to 18 in which one or more hydrogen atoms may be substituted by a halogen atom and R is an aliphatic group having a carbon number of from 1 to 18, which may be substituted by one or more halogen atom(s). Preferably, R is an aliphatic group having a carbon number of from 1 to 6 and, more preferably, an aliphatic group having a carbon number of from 1 to 4, which is substituted by at least one fluorine atom. Examples of such PAG compounds include those in Table 1:

TABLE 1

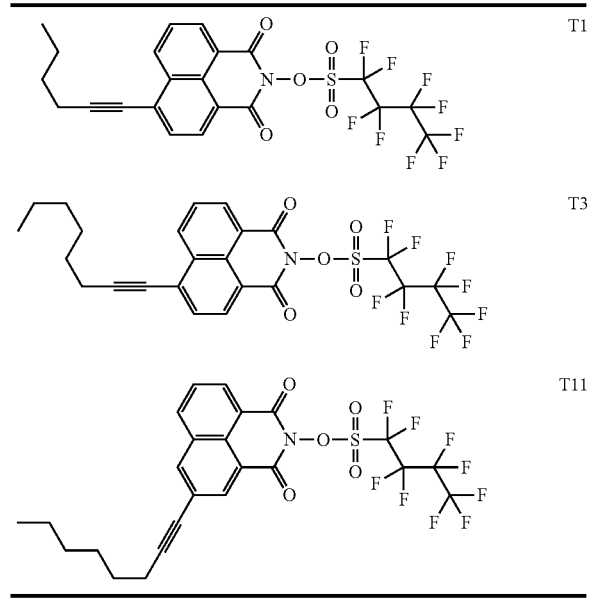

In other embodiments, R⁰ in Formulas (I) and (II) is an aliphatic group having a carbon number of from 2 to 18 which comprises at least one —C(=O)—O— moiety. In an embodiment, R⁰ in Formulas (I) and (II) is an aliphatic group having a carbon number of from 2 to 18 which comprises at least one —C(=O)—O— moiety and R is an aliphatic group having a carbon number of from 1 to 18, which may be substituted by one or more halogen atom(s). Preferably, R is an aliphatic group having a carbon number of from 1 to 6 and, more preferably, an aliphatic group having a carbon number of from 1 to 4, which is substituted by at least one fluorine atom. Examples of such PAG compounds include those in Table 2:

TABLE 2

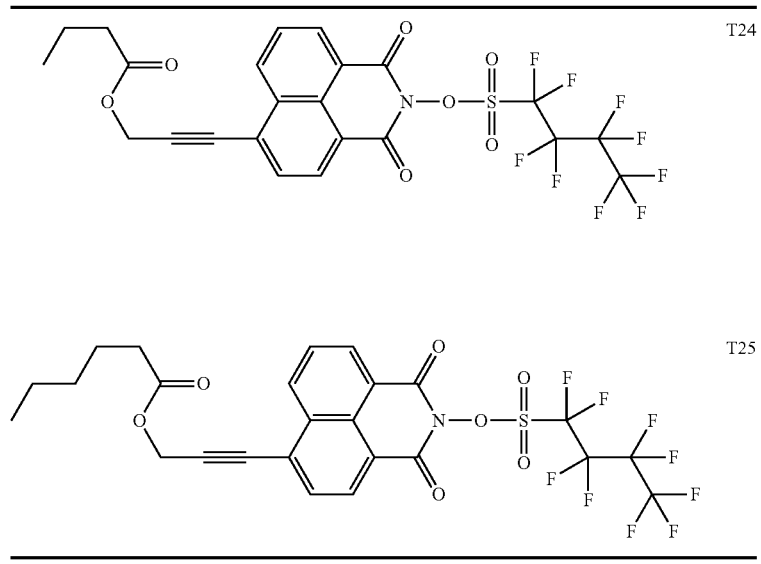

In yet other embodiments, R⁰ in Formulas (I) and (II) is an aliphatic group having a carbon number of from 1 to 18 in which one or more hydrogen atoms may be substituted by a halogen atom. In another embodiment, R⁰ in Formulas (I) and (II) is an aliphatic group having a carbon number of from 1 to 18 in which one or more hydrogen atoms may be substituted by a halogen atom and R is an aryl or heteroaryl group having a carbon number of from 4 to 18 in which one or more hydrogen atoms may be substituted by a halogen atom, an aliphatic group, or a haloalkyl group. Examples of such PAG compounds include those in Table 3:

TABLE 3

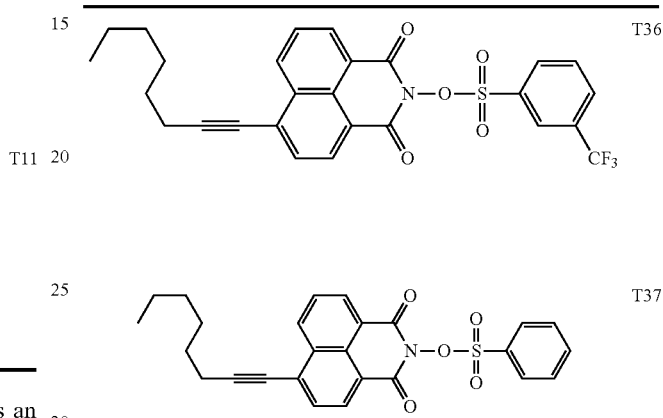

In the most preferred embodiments of Formulas (I) and (II) according to the invention, R is —CF₃. In such embodiments the above-recited proviso applies. Preferred embodiments include compounds where R⁰ is a group represented by the Formula (A): —CH₂—R¹¹ (A), wherein R¹¹ is selected from the group consisting of an aliphatic group having a carbon number of from 4 to 18. Examples include n-butyl, iso-butyl, sec-butyl, tert-butyl, n-pentyl, n-hexyl, 2-ethylhexyl, n-heptyl, n-octyl, n-nonyl, and n-decyl. Examples of such preferred PAG compounds include those in Table 4:

TABLE 4
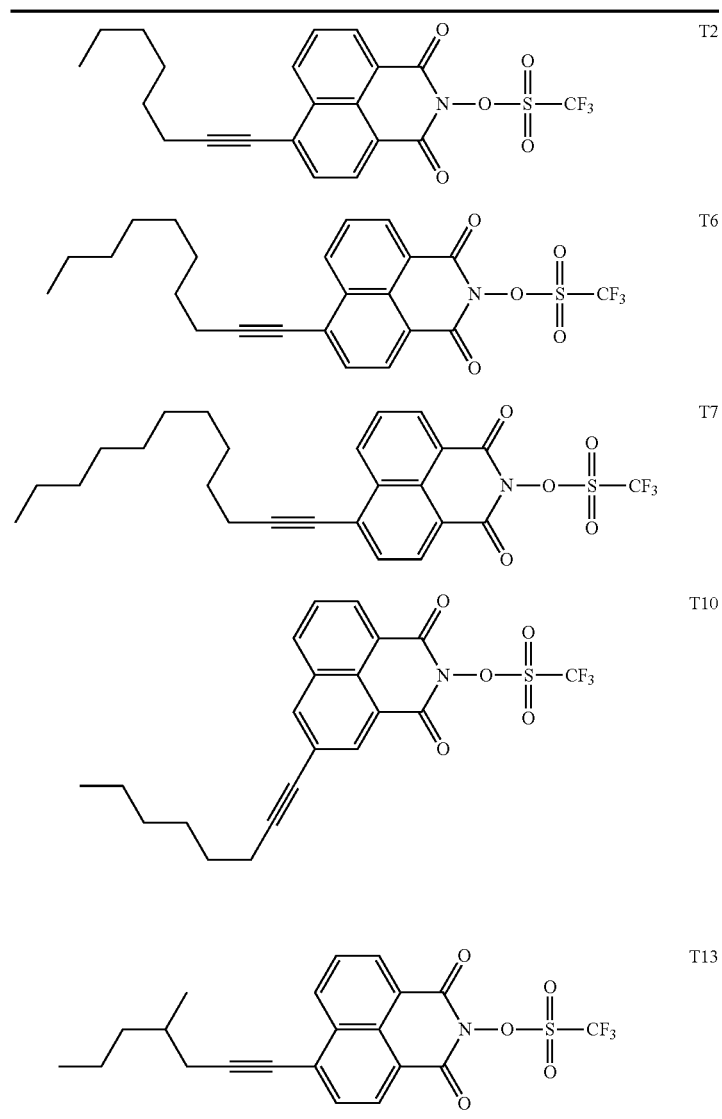
In other preferred embodiments where R is —CF₃ in Formulas (I) and (II), R⁰ is an aliphatic group having a carbon number of from 2 to 18 which comprises at least one —C(=O)—O— or —O—C(=O)—O— moiety, wherein the aliphatic group optionally comprises at least one halogen atom. Examples of such preferred PAG compounds include those in Table 5:
TABLE 5
TABLE 5-continued
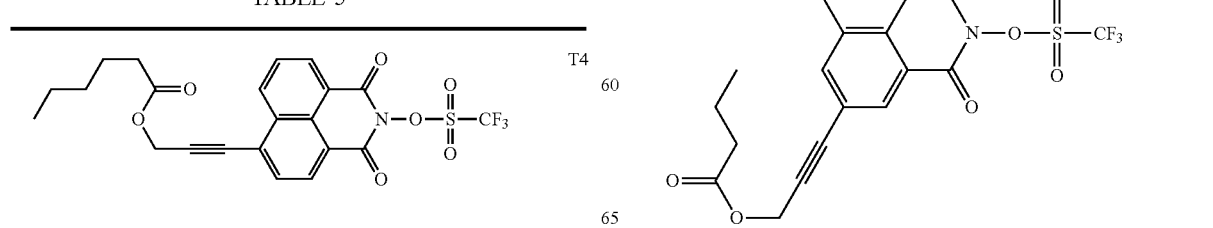

TABLE 5-continued
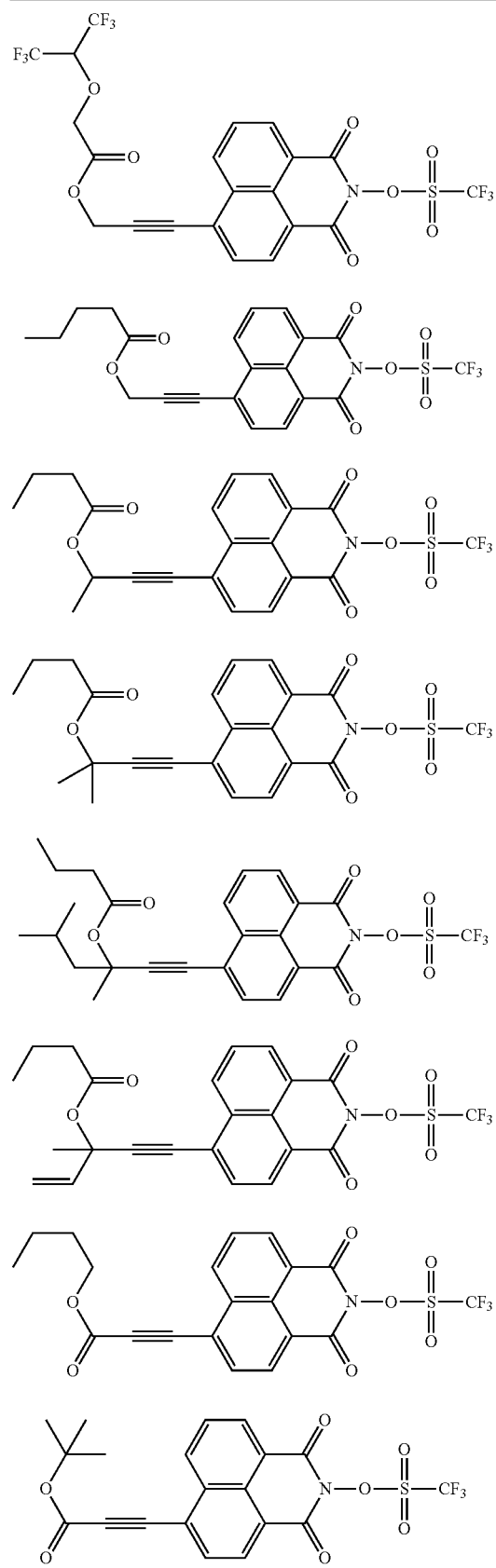
TABLE 5-continued
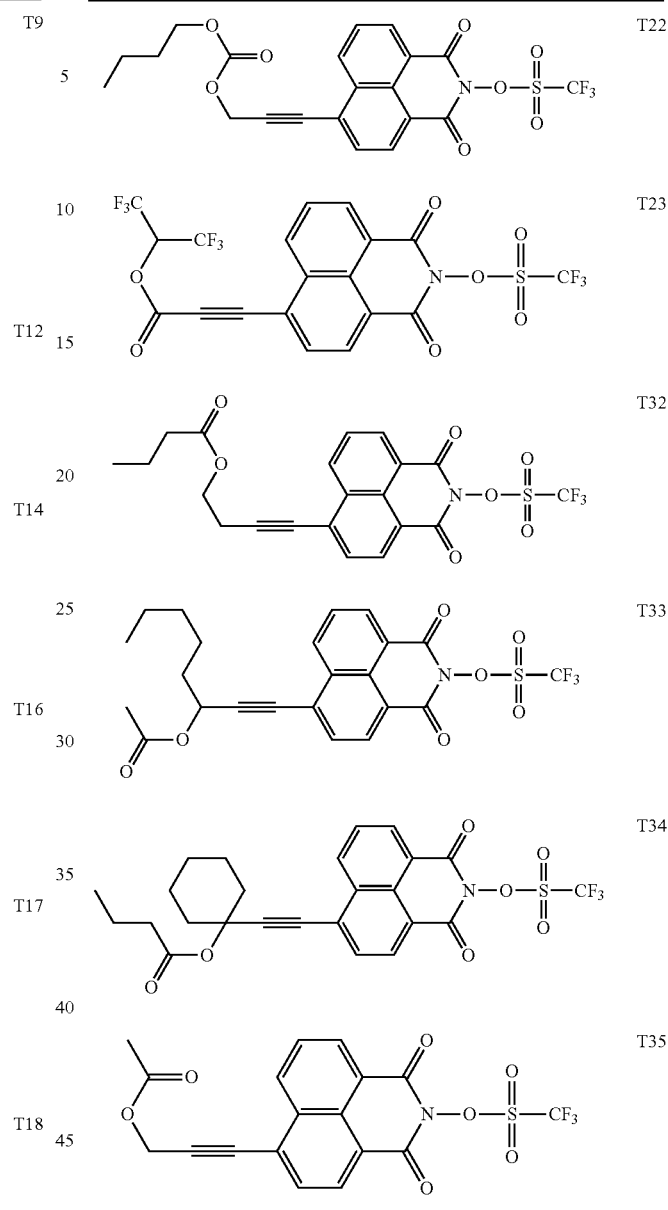
In yet other preferred embodiments where R is —CF$_3$ in Formulas (I) and (II), R$^0$ is an aliphatic group having a carbon number of from 2 to 18 which comprises at least one —O—, —S—, or —C(=O)— moiety, wherein the aliphatic group optionally comprises at least one halogen atom. Examples of such preferred PAG compounds include those in Table 6:
TABLE 6
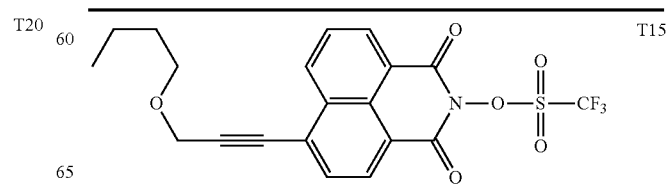

TABLE 6-continued

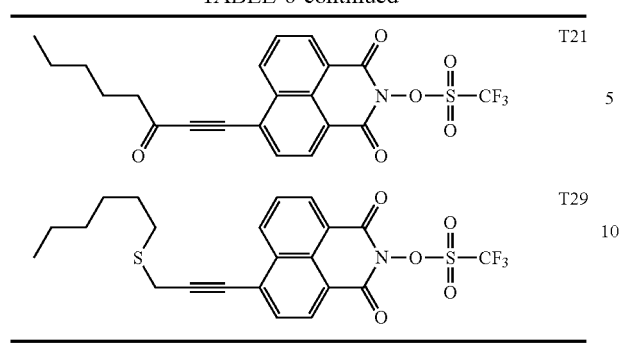

In yet other preferred embodiments where R is —$CF_3$ in Formulas (I) and (II), $R^o$ is an aliphatic group having a carbon number of from 2 to 18 which comprises at least one —C(=O)—S—, —C(=O)—NH—, —O—C(=O)—NH—, —C(=O)—$NR_a$—, —O—C(=O)—$NR_a$—, or —C(=O)—$NR_aR_b$ moiety, wherein $R_a$ and $R_b$ are as defined above, and wherein the aliphatic group optionally comprises at least one halogen atom. Examples of such preferred PAG compounds include those in Table 7:

TABLE 7

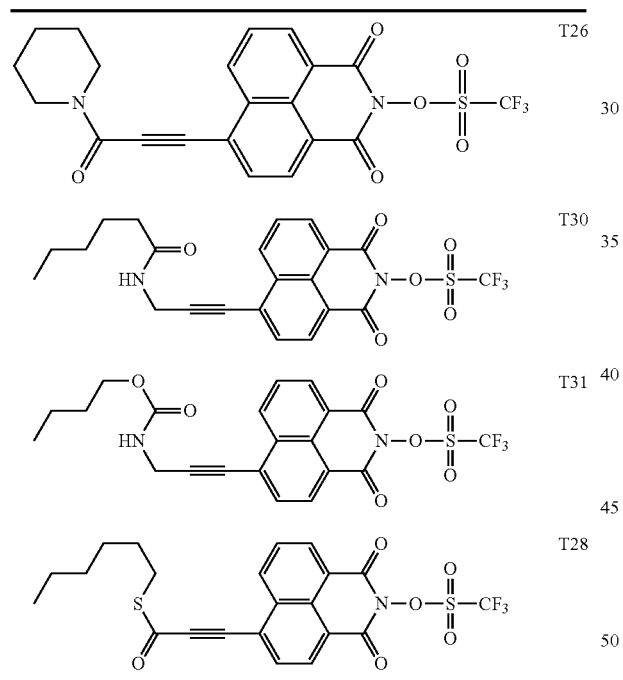

In another preferred embodiment where R is —$CF_3$ in Formulas (I) and (II), $R^o$ is a group represented by the Formula (B):

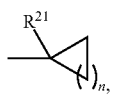
(B)

wherein $R^{21}$ is selected from the group consisting of a hydrogen atom or an alkyl group having a carbon number of from 1 to 10; and n is equal to 1 to 5. An example of such PAG compound is compound T27

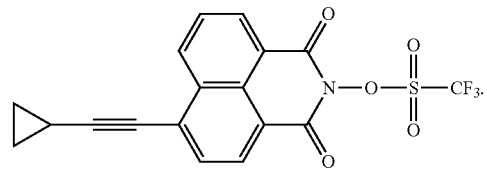

In other embodiments of the invention, both R and $R^o$ in Formulas (I) and (II) are an aliphatic group having a carbon number of from 1 to 18. Examples of such PAG compounds include compounds T38 and T40:

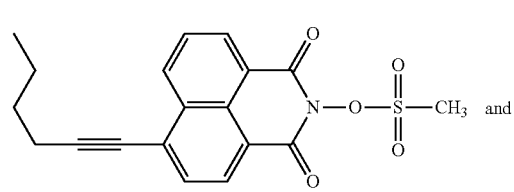

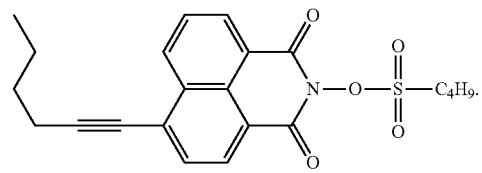

In other embodiments of the invention, R in Formulas (I) and (II) is an aliphatic group having a carbon number of from 2 to 18 which comprises at least one —C(=O)— moiety and $R^o$ in Formulas (I) and (II) is an aliphatic group having a carbon number of from 1 to 18. Examples of such PAG compounds include compound T39:

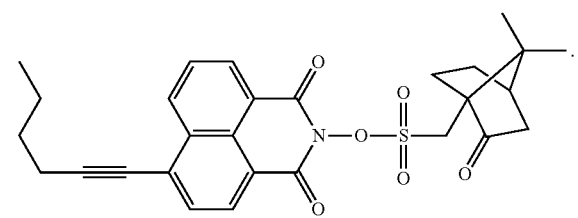

PAGs according to the invention impart a high degree of efficiency to the photolithography process and leads to enhanced contrast and resolution between exposed and unexposed regions of the resist composition. The amount of PAG and the energy supplied by the UV irradiation are chosen such that they are sufficient to allow the desired polycondensation.

PAGs of the invention may be suitably used in positive-acting or negative-acting chemically amplified photoresists, i.e., negative-acting resist compositions which undergo a photoacid-promoted cross-linking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions.

Preferred imaging wavelengths for photoresists of the invention include sub-300 nm wavelengths, e.g., 248 nm, and sub-200 nm wavelengths, e.g., 193 nm and EUV, more preferably in the range from 200 to 500 nm, preferably in the range from 300 to 450 nm, even more preferably in the range from 350 to 440 nm, most preferably at wavelengths of 365 nm (i-line), 405 (h-line) and 436 nm (g-line).

Preparation of Compounds of Formulas (I) and (II) (Further Details in the Examples)

There is no particular limitation for the method for producing the N-hydroxynaphthalimide sulfonate derivative compounds of the invention, and any known synthesis can be used to make the compounds of Formulas (I) and (II). There is no particular limitation for the method for producing the N-hydroxynaphthalimide sulfonate derivative compounds, and any well-known approach can be used for the synthesis of these compounds. Two typical routes that we adopted to synthesize triflate compounds are illustrated in Scheme 1. Compounds with a triple-bond substituent at 3 position can be similarly synthesized by starting from 3-bromo anhydride. The starting anhydrides (4-bromo-1,8-naphthalic anhydride and 3-bromo-1,8-naphthalic anhydride) are commercially available.

As shown in Scheme 1, Sonagashira coupling between 4-bromo-1,8-naphthalic anhydride and a terminal alkyne affords naphthalic anhydrides with a triple-bond substituent. These anhydrides are converted to the final N-hydroxynaphthalimide sulfonate derivatives via two different approaches. The first approach involves an one-pot reaction using 2.2 equivalents of triflic anhydride. The second approach allows for the isolation of N-hydroxyl imide intermediates and only 1.2 equivalent of triflic anhydride is required.

may be base soluble or insoluble; (iii) an organic solvent; and, optionally, (iv) an additive.

Photoresist compositions according to the invention comprising the photoacid generators of Formulas (I) and (II) are suitable for use as a photoresist in a variety of applications, in particular for the production of electronic devices, including flat panel display (in this case the photoresist can be coated glass substrate or a layer of indium tin oxide) and a semiconductor device (in this case the photoresist can be coated onto a silicon wafer substrate). Various exposure radiations can be used, including an exposure with electromagnetic radiation having a wavelength of 200 to 500 nm, preferably in the range from 300 to 450 nm, more preferably in the range from 350 to 440 nm, even more preferably at 365 nm (i-line), 436 nm (g-line) or 405 nm (h-line), wherein an electromagnetic radiation with a wavelength of 365 nm is particularly preferred.

The photoresist compositions according to the invention comprise as component (ii) one or more photoresist polymers or copolymers, which may be soluble or insoluble in a developer solution. The photoresist compositions according to the invention may be for positive tone or negative tone composition. In the case of a positive tone composition the solubility of component (ii) is increased upon reaction with the acid released from the compound according to the invention. In this case, photoresist polymers or copolymers with acid labile groups are used as component (ii) which are insoluble in aqueous base solution, but which in the presence of the acid are catalytically de-protected such that they become soluble in solution. In the case of a negative tone composition, the solubility of component (ii) is decreased upon reaction with the acid released from the compound according to the invention. In this case, photoresist polymers or copolymers are used as component (ii) which are soluble in the developer solution, but are cross-linked in the presence of the acid such that they become insoluble in an aqueous base solution. Thus, photoresist polymers or copolymers are capable of being imparted with an altered solubility in a developer solution in the presence of an acid.

Scheme 1.

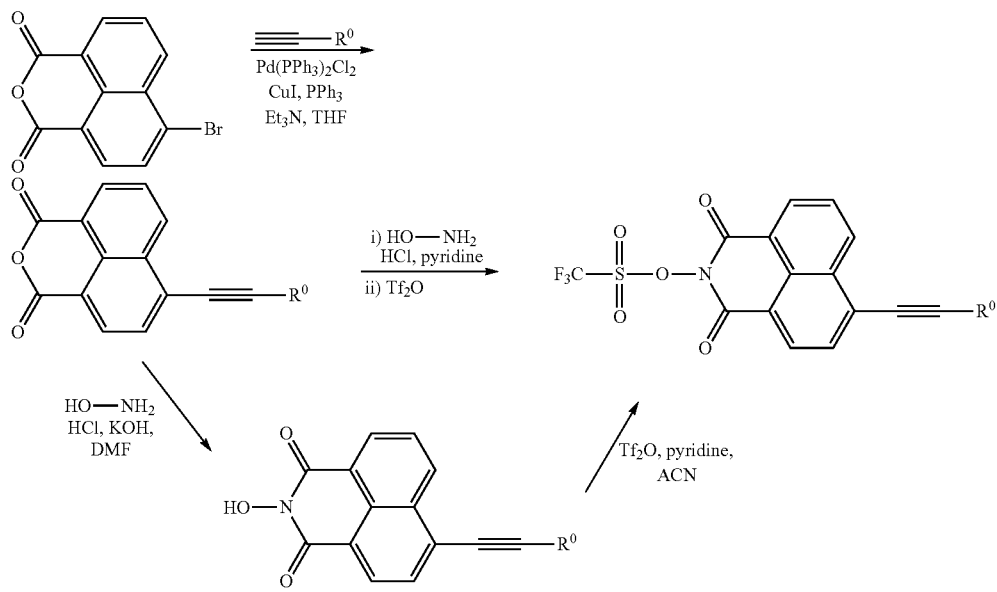

Photoresist Compositions

Photoresist compositions of the invention comprise (i) at least one photoacid generator selected from Formula (I) and (II); (ii) at least one photoresist polymer or copolymer which Preferably the developer solution is an aqueous solution, more preferably it is an aqueous base solution.

Examples of photoresist polymers that may be used as component (ii) in a positive tone composition include without limitation, aromatic polymers, such as homopolymers or copolymers of hydroxystyrene protected with an acid labile group; acrylates, such as for example, poly(meth)acrylates with at least one unit containing a pendant alicyclic group, and with the acid labile group being pendant from the polymer backbone and/or from the aclicyclic group, cycloolefin polymers, cycloolefin maleic anhydride copolymers, cycloolefin vinyl ether copolymers, siloxanes; silsesquioxanes, carbosilanes; and oligomers, including polyhedral oligomeric silsesquioxanes, carbohydrates, and other cage compounds. The foregoing polymers or oligomers are appropriately functionalized with aqueous base soluble groups, acid-labile groups, polar functionalities, and silicon containing groups as needed.

Examples of copolymers that may be used as component (ii) in the positive tone compositions of the invention include without limitation poly(p-hydroxystyrene)-methyl adamantyl methacrylate (PHS-MAdMA), poly(p-hydroxystyrene)-2-ethyl-2-adamantyl methacrylate (PHS-EAdMA), poly(p-hydroxystyrene)-2-ethyl-2-cyclopentyl methacrylate (PHS-ECpMA), poly(p-hydroxy-styrene)-2-methyl-2-cyclopentyl methacrylate (PHS-MCpMA) or PHS-EVE.

Preferably, the at least one component (ii) in a positive tone composition is a poly(hydroxystyrene)-resin in which at least a part of the hydroxy groups is substituted by protective groups. Preferred protective groups are selected from the group consisting of a tert-butoxycarbonyloxy group, a tert-butyloxy group, a tert-amyloxycarbonyloxy group and an acetal group. Furthermore suitable as component ii) are all the polymers and copolymers which in paragraphs [0068] to [0114] of EP 1 586 570 A1 are described as "acid-dissociable group-containing resin." The disclosure of EP 1 586 570 A1 with respect to these resins is incorporated herein by reference a forms a part of the disclosure of the invention.

Preferred negative tone compositions comprise a mixture of materials that will cure, crosslink or harden upon exposure to acid. Preferred negative acting compositions comprise, as component (ii), a polymer binder such as a phenolic or non-aromatic polymer, a cross-linker component as an additive (iv) and the photoacid generator component according to the invention as component (i). Suitable polymer binders and cross-linkers for such negative tone photoresist compositions and the use thereof have been disclosed in EP-A-0 164 248 and U.S. Pat. No. 5,128,232. Preferred phenolic polymers for use as component (ii) include novolaks and poly(vinylphenol)s. Novolak resins are the thermoplastic condensation products of a phenol and an aldehyde. Examples of suitable phenols for condensation with an aldehyde, especially formaldehyde, for the formation of novolak resins include phenol, m-cresol, o-cresol, p-cresol, 2,4-xylenol, 2,5-xylenol, 3,4-xylenol, 3,5-xylenol and thymol. An acid catalyzed condensation reaction results in the formation of a suitable novolak resin which may vary in molecular weight from about 500 to 100,000 Daltons. Polyvinyl phenol resins are thermoplastic polymers that may be formed by block polymerization, emulsion polymerization or solution polymerization of the corresponding monomers in the presence of a cationic catalyst. Vinylphenols useful for the production of polyvinyl phenol resins may be prepared, for example, by hydrolysis of commercially available coumarin or substituted coumarins, followed by decarboxylation of the resulting hydroxy cinnamic acids. Useful vinylphenols may also be prepared by dehydration of the corresponding hydroxy alkyl phenols or by decarboxylation of hydroxy cinnamic acids resulting from the reaction of substituted or non-substituted hydroxybenzaldehydes with malonic acid. Preferred polyvinyl phenol resins prepared from such vinylphenols have a molecular weight range of from about 2,000 to about 60,000 daltons. Preferred cross-linkers for use as component (iv) include amine-based materials, including melamine, glycolurils, benzoguanamine-based materials and urea-based materials. Melamine-formaldehyde polymers are often particularly suitable. Such cross-linkers are commercially available, e.g., the melamine polymers, glycoluril polymers, urea-based polymer and benzoguanamine polymers, such as those sold by Cytec under trade names Cymel™ 301, 303, 1170, 1171, 1172, 1123 and 1125 and Beetle™ 60, 65 and 80.

As component (iii) the composition according to the invention comprises at least one organic solvent. The organic solvent may be any solvent capable of dissolving the component (ii) and the component (i) to generate a uniform solution, and one or more solvents selected from known materials used as the solvents for conventional chemically amplified resists can be used. Specific examples of the organic solvent include ketones such as acetone, methyl ethyl ketone, cyclohexanone, methyl isoamyl ketone and 2-heptanone, polyhydric alcohols and derivatives thereof such as ethylene glycol, ethylene glycol monoacetate, diethylene glycol, diethylene glycol monoacetate, propylene glycol, propylene glycol monoacetate, dipropylene glycol, or the monomethyl ether, monoethyl ether, monopropyl ether, monobutyl ether or monophenyl ether of dipropylene glycol monoacetate, cyclic ethers such as dioxane, and esters such as methyl lactate, ethyl lactate (EL), methyl acetate, ethyl acetate, butyl acetate, methyl pyruvate, ethyl pyruvate, methyl methoxypropionate, and ethyl ethoxypropionate. These organic solvents can be used alone, or as a mixed solvent containing two or more different solvents. Particularly preferred organic solvents (iii) are selected from the group consisting of a ketone, an ether and ester.

Furthermore, the composition according to the invention may also, optionally, comprise at least one additive being different from components (i), (ii) and (iii). For example, other optional additives include actinic and contrast dyes, anti-striation agents, plasticizers, speed enhancers, sensitizers, etc. Such optional additives typically will be in minor concentration in a photoresist composition except for fillers and dyes which may be in relatively large concentrations such as, e.g., in amounts of from 5 to 30 percent by weight of the total weight of a resist's dry components.

One additive typically employed in photoresist compositions according to the invention is a basic quencher. The basic quencher is for purposes of neutralizing acid generated in the surface region of the underlying photoresist layer by stray light which reaches what are intended to be unexposed (dark) regions of the photoresist layer. This allows for improvement in depth of focus in the defocus area and exposure latitude by controlling unwanted deprotection reaction in the unexposed areas. As a result, irregularities in the profile, for example, necking and T-topping, in formed resist patterns can be minimized or avoided.

To allow for effective interaction between the basic quencher and the acid generated in the dark areas of the underlying photoresist layer, the basic quencher should be of a non-surfactant-type. That is, the basic quencher should not be of a type that migrates to the top surface of the overcoat layer due, for example, to a low surface free energy relative to other components of the overcoat composition. In such a case, the basic quencher would not be appreciably at the photoresist layer interface for interaction with the generated acid to prevent acid deprotection. The basic quencher should therefore be of a type that is present at the overcoat layer/photoresist layer interface, whether being uniformly dispersed through the overcoat layer or forming a graded or segregated layer at the interface. Such a segregated layer can be achieved by selection of a basic quencher having a high surface free energy relative to other components of the overcoat composition.

Suitable basic quenchers include, for example: linear and cyclic amides and derivatives thereof such as N,N-bis(2-hydroxyethyl)pivalamide, N,N-Diethylacetamide, N1,N1,N3,N3-tetrabutylmalonamide, 1-methylazepan-2-one, 1-allylazepan-2-one and tert-butyl 1,3-dihydroxy-2-(hydroxymethyl)propan-2-ylcarbamate; aromatic amines such as pyridine, and di-tert-butyl pyridine; aliphatic amines such as triisopropanolamine, n-tert-butyldiethanolamine, tris(2-acetoxy-ethyl)amine, 2,2',2'',2'''-(ethane-1,2-diylbis(azanetriyl))tetraethanol, and 2-(dibutylamino)ethanol, 2,2',2''-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate and N (2-acetoxy-ethyl)morpholine. Of these basic quenchers, 1-(tert-butoxycarbonyl)-4-hydroxypiperidine and triisopropanolamine are preferred. While the content of the basic quencher will depend, for example, on the content of the photoacid generator in the underlying photoresist layer, it is typically present in an amount of from 0.1 to 5 wt %, preferably from 0.5 to 3 wt %, more preferably from 1 to 3 wt %, based on total solids of the overcoat composition.

Another concept is to attach a basic moiety to the PAG molecule. In this case the quencher is a part of the PAG and in close proximity to the acid formed upon irradiation. These compounds have a high sensitivity towards electromagnetic radiation, in particular towards electromagnetic radiation with a wavelength in the range of 200 to 500 nm, more particularly towards electromagnetic radiation with a wavelength of 365 nm (i-line), and—at the same time—allows the production of a patterned structure with a higher resolution, compared to the photoresist compositions known from the prior art containing quenchers as additives. Compounds that follow this concept are for example T26, T30, and T31.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

According to a preferred embodiment, the compositions according to the invention comprise:
(i) 0.05 to 15 wt. %, preferably 0.1 to 12.5 wt. % and most preferably 1 to 10 wt. % of at least one photoacid generator compound of Formula (I) or (II);
(ii) 5 to 50 wt. %, preferably 7.5 to 45 wt. % and most preferably 10 to 40 wt. % of at least one photoresist polymer or copolymer which may be base soluble or insoluble; and
(iv) 0 to 10 wt. %, preferably 0.01 to 7.5 wt. % and most preferably 0.1 to 5 wt. % of the further additive, wherein the reminder in the composition is the organic solvent (iii).

As in the compounds according to the invention the functional basic group serving as a quencher for the acid group that is released upon exposure to electromagnetic radiation is a part of the photoacid generator compound, it is not necessary to add a separate basic component as a quencher (as it is necessary in the photoresist compositions known from the prior art). According to a preferred embodiment of the composition according to the invention this composition preferably comprises less than 5 wt. %, more preferably less than 1 wt. %, even more preferably less than 0.1 wt. %, and most preferably 0 wt. % of a basic compound being different from components (i) through (iv), such as hydroxides, carboxylates, amines, imines, and amides.

The photoresists of the invention are generally prepared following known procedures with the exception that a PAG of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether; lactates such as ethyl lactate or methyl lactate, with ethyl lactate being preferred; propionates, particularly methyl propionate and ethyl propionate; a Cellosolve ester such as methyl Cellosolve acetate; an aromatic hydrocarbon such as toluene or xylene; or a ketone such as methylethyl ketone, cyclohexanone and 2-heptanone. Typically the solids content of the photoresist varies between 5 and 35 percent by weight of the total weight of the photoresist composition.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and non-exposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, e.g., glass substrates, indium tin oxide coated substrates and the like. A liquid coating resist composition may be applied by any standard means such as spinning, dipping or roller coating. The exposure energy should be sufficient to effectively activate the photoactive component of the radiation sensitive system to produce a patterned image in the resist coating layer. Suitable exposure energies typically range from about 1 to 300 mJ/cm$^2$. As discussed above, preferred exposure wavelengths include sub-200 nm such as 193 nm. Suitable post-exposure bake temperatures are from about 50° C. or greater, more specifically from about 50 to 140° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

Composites

The invention provides a process for producing a composite comprising a substrate and a coating that is applied onto the substrate in a patterned structure, the process comprising the steps of:

(a) applying a layer of the composition according to the invention onto the surface of the substrate and at least partial removal of the organic solvent (iii);

(b) exposing selected areas of the layer to electromagnetic radiation, thereby releasing an acid from the compound (i) in the areas exposed to the electromagnetic radiation;

(c) optionally heating the layer to impart compound (ii) in the areas in which the acid has been released with an altered solubility in an aqueous solution; and (d) at least partial removal of the layer.

In process step (a), a layer of the composition according to the invention is applied onto the surface of the substrate followed by at least partial removal of the organic solvent (iii).

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Application of the composition according to the invention onto the substrate may be accomplished by any suitable method, including spin coating, spray coating, dip coating, doc-tor blading, or the like. Applying the layer of photoresist is preferably accomplished by spin-coating the photoresist using a coating track, in which the photoresist is dispensed on a spinning wafer. During the spin coating process, the wafer may be spun at a speed of up to 4,000 rpm, preferably from about 500 to 3,000 rpm, and more preferably 1,000 to 2,500 rpm. The coated wafer is spun to remove the organic solvent (iii), and baked on a hot plate to remove residual solvent and free volume from the film to make it uniformly dense.

In process step (b), selected areas of the layer are exposed to electromagnetic radiation, there-by releasing an acid from the compound (i) in the areas exposed to the electromagnetic radiation. As stated above, various exposure radiations can be used, including an exposure with electromagnetic radiation having a wavelength of 365 nm (i-line), 436 nm (g-line) or 405 nm (h-line), wherein electromagnetic radiation having a wavelength of 365 nm is particularly preferred.

Such a pattern-wise exposure can be carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the component according to the invention that is contained in the photoresist layer in the exposed areas and generates acid and decomposition by-products, and that the acid then effects a chemical change in the polymer compound (ii) (de-blocking the acid sensitive group to generate a base-soluble group, or alternatively, catalyzing a cross-linking reaction in the exposed areas). The resolution of such exposure tools may be less than 30 nm.

In process step (c), the layer can optionally be is heated to impart compound (ii) in the areas in which the acid has been released with an altered solubility in an aqueous solution. In this so called "post-exposure bake" the solubility differences between exposed and unexposed regions of the coating layer are created or enhanced. Typically post-exposure bake conditions include temperatures of about 50° C. or greater, more specifically a temperature in the range of from about 50° C. to about 160° C. for 10 seconds to 30 minutes, preferably for 30 to 200 seconds. According to a particular embodiment of the process according to the invention no heat treatment is performed after process step (b) and before (d).

In process step (d) the layer is at least partially removed with an aqueous solution, preferably an aqueous base solution. This can be accomplished by treating the exposed photoresist layer with a suitable developer capable of selectively removing the exposed portions of the film (where the photoresist is positive tone) or removing the unexposed portions of the film (where the photoresist is negative tone). Preferably, the photoresist is positive tone based on a polymer having acid sensitive (de-protectable) groups, and the developer is preferably a metal-ion free tetraalkylammonium hydroxide solution.

The composite made according to the invention is characterized in that it comprises a substrate and a coating applied on the surface of the substrate in a patterned structure, wherein the coating comprises a compound according to the invention.

The use of the photoacid generator compounds of Formula (i) and (II) for photo-induced polymerization, photo-induced cross-linking, photo-induced degradation and photo-induced transformation of functional groups is also within the scope of the invention. The compound according to the invention is particularly suitable for use in protective coatings, smart cards, 3D rapid prototyping or additive manufacturing, sacrificial coatings, adhesives, antireflective coatings, holograms, galvano- and plating masks, ion implantation masks, etch resists, chemical amplified resists, light sensing applications, PCB (printed circuit board) patterning, MEMS fabrication, TFT layer pattering on flat panel display, TFT layer pattering on flexible display, pixel pattering for display, in color filters or black matrix for LCD, or semiconductor patterning in packaging process and TSV related patterning on semiconductor manufacturing protective coatings, smart cards, 3D rapid prototyping or additive manufacturing, sacrificial coatings, adhesives, antireflective coatings, holograms, galvano- and plating masks, ion implantation masks, etch resists, chemical amplified resists, light sensing applications or in color filters.

The following Examples are intended to illustrate the above invention and should not be construed as to narrow its scope. One skilled in the art will readily recognize that the Examples suggest many other ways in which the invention could be practiced. It should be understood that many variations and modifications may be made while remaining within the scope of the invention.

EXAMPLES

Solubility

Solubility is an important factor in the evaluation of a PAG. High solubility not only makes a PAG purified readily but also enables a PAG to be used for a wide range of concentrations in photoresists and in varied solvent systems. To test the solubility of a PAG, a solvent is slowly added until the PAG is completely dissolved and no turbidity is observed in the clear solution. Table 8 lists the solubility (w/w %) of some representative N-hydroxynaphthalimide sulfonate derivatives versus NIT in various organic solvents at 20° C. All compounds of the invention exhibit much higher solubility in PGMEA and cyclohexanone than comparative compounds A and B and the commercial benchmark (NIT). It should be noted that compounds T2 and T5 exhibit extremely high solubility in the tested solvents. These results indicate that the N-hydroxynaphthalimide sulfonate derivatives in the current invention may be used at high concentration in a photosensitive composition. Since the solubility of a PAG varies significantly with the change of temperature, high solubility improves the solution stability of the photosensitive composition so that the composition can be allowed for a wide range of operating temperatures without worrying about recrystallization of the PAG from the composition.

TABLE 8

| Compound | Solubility (w/w%) | | |
| --- | --- | --- | --- |
| | PGMEA* | Cyclohexanone | GBL** |
| NIT | 1.7% | 5.9% | 2.2% |
| Comparative A | 1.0% | 3.5% | 0.9% |
| Comparative B | 6.1% | 11.5% | 2.3% |
| T1 | 8.3% | 19.7% | 1.5% |
| T2 | 45.8% | 52.4% | 23.1% |

TABLE 8-continued

| Compound | Solubility (w/w%) | | |
|---|---|---|---|
| | PGMEA* | Cyclohexanone | GBL** |
| T3 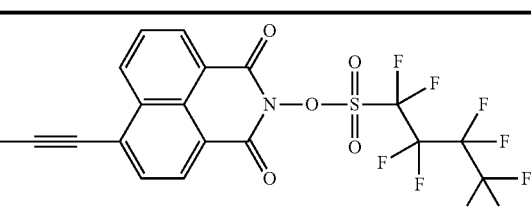 | 20.6% | 42.0% | 2.2% |
| T5 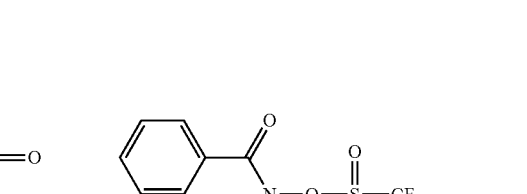 | 50.1% | 55.4% | 32.4% |

*Propylene glycol monomethyl ether acetate
**γ-Butyrolactone

Photoreactivity

A photoresist composition typically comprises PAG, polymers, additives and solvents. The performance of a photoresist composition is mainly dependent on the properties of the PAG and polymer components. To formulate a high-performance photoresist composition, more photosensitive PAGs are typically selected. The photosensitivity of a PAG is typically directly related to the strength of the generated acid and the photoreactivity of the PAG. For a series of PAGs producing the same latent acid, their photosensitivity is related only to their photoreactivity. Thus evaluating the photosensitivity of a PAG can be achieved by studying its photoreactivity. The higher photoreactivity, the higher photosensitivity. The photoreactivity can be investigated by photolysis of a PAG in its dilute solution under low exposure intensity (to avoid side reactions which don't generate the desired acid). The change in the concentration of a PAG upon irradiation can be determined by measuring the absorbance of the PAG at the maximum absorption wavelength.

Photolysis of PAGs was carried out in acetonitrile in air at room temperature. The sodium salt of tetrabromophenol blue (TBPBNa), an acid indicator dye, which has a maximum absorption at 618 nm, was purchased from Aldrich (indicator grade) and used as received. Irradiation of the solution of the PAGs ($3\times10^{-5}$ M) was performed using a Cole-Parmer UV 15 W bench lamp (EW-97605-50) at 365 nm. Light intensity was measured using an UV Power Puck II radiometer from EIT Inc. UV-Vis spectra were run on a Thermo Scientific Evolution 201 UV-visible spectrophotometer.

Figure 2:
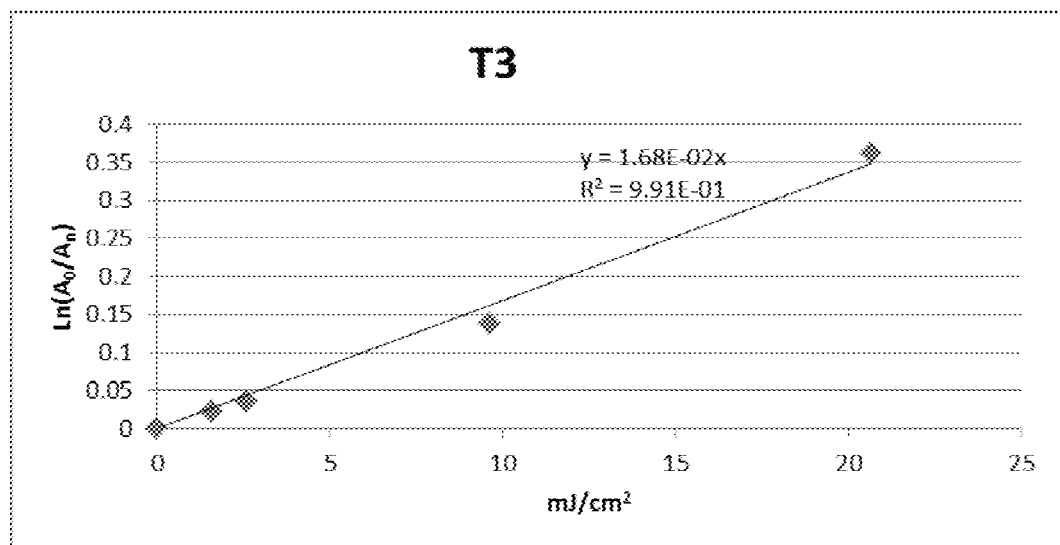
FIG. 2 is a plot of the natural log of the changes in absorbance with exposure dose of energy from the spectra of FIG. 1 to give the photoreaction constant of T3.

Photolysis of NIT, comparative compound A and B, T1, T2, T3, and T5 was examined in acetonitrile. Referring to FIG. 1, the UV-Vis spectral changes of T3 upon irradiation with a UV lamp at 365 nm, shows the decrease of the intensity with the increase of exposure dose of energy ($mJ/cm^2$). The absorption band at 362 nm ($\lambda_{max}$) gradually decreases upon irradiation, indicating the progress of photoreaction with the increase of exposure dose of energy. Assuming the photoreaction is first-order, a plot of the natural log of changes in absorbance with exposure dose of energy gives the photoreaction constant of T3 (i.e., the slope of the linear trendline) (FIG. 2). The photoreaction constants of other compounds were similarly determined under the same irradiation condition. Comparing the constants of A, B, T1, T2, T3, and T5 with that of NIT normalized to one gives the relative photoreactivity (Table 9). The photoreactivity for PAGs (T1, T2 and T3) according to this invention is 8 to 10 times greater than that of NIT and 3 to 4 times greater than that of Comparative Compound A. The PAG (T1 and T3) with a nonaflate group is more photoreactive than those with a triflate group. The formation of acid upon irradiation was confirmed by observing the spectral changes of the acid indicator, TBPBNa at 618 nm.

TABLE 9
Comparison of solubility and photoreactivity.
| PAG | Solubility (w/w%) in PGMEA* | Relative Photoreactivity at 365 nm | Solubility × Photoreactivity |
|---|---|---|---|
| 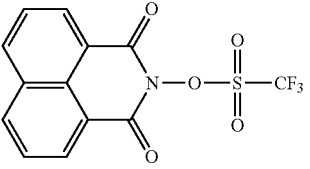 NIT** | 1.7% | 1.0 | 1.7% |
| 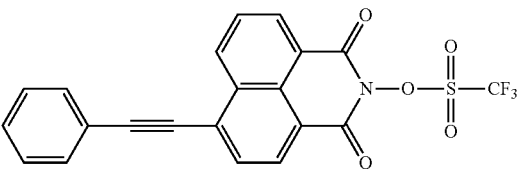 Comparative Compound A | 1.0% | 2.5 | 2.5% |
| 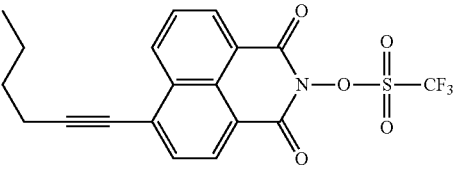 Comparative Compound B | 6.1% | 8.0 | 48.8% |
| 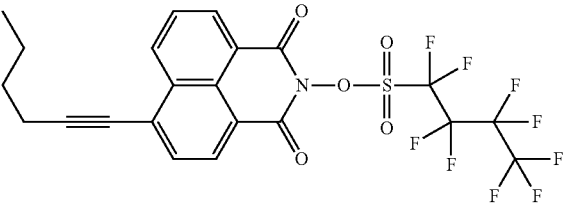 T1 | 8.3% | 9.3 | 77.2% |
| 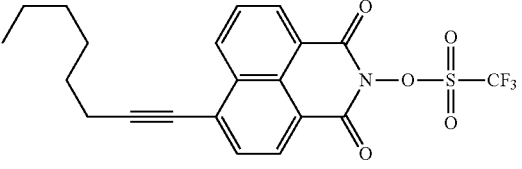 T2 | 45.8% | 8.6 | 394% |
| 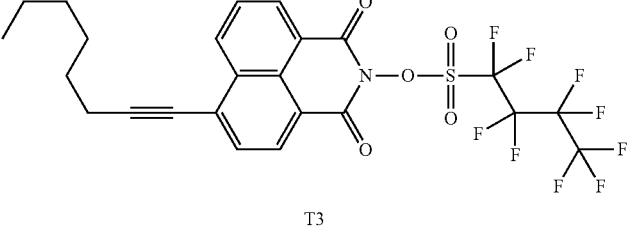 T3 | 20.6% | 9.6 | 198% |

TABLE 9-continued

Comparison of solubility and photoreactivity.

| PAG | Solubility (w/w%) in PGMEA* | Relative Photoreactivity at 365 nm | Solubility × Photoreactivity |
|---|---|---|---|
| 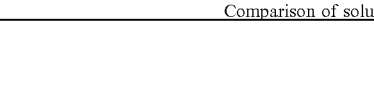 T5 | 50.1% | 4.0 | 200% |

*= Propylene glycol monomethyl ether acetate
**= N-Hydroxynaphthalimide triflate (NIT)

Resist Evaluation

Referring to Table 10, four different photoresist compositions according to this invention were prepared by following this general procedure: 50 g of PHS-EVE polymer solution (~30 wt % polymer content in PGMEA; ca. 35% of the OH groups blocked with EVE, Mw=32,000, Mw/Mn=1.88) and 50 g of PGMEA are pre-mixed. To this mixture are added 1.3 mmol of a PAG and 0.0263 g (20 mol % of the PAG) of triethylamine was used as a quencher. The mixture was stirred until the solid was completely dissolved. The compositions were then stored in darkness for subsequent pattern studies by photolithography.

TABLE 10

Composition Summary and Exposure

| Photoresist composition | PAG | PAG amount (1.3 mmol) | Proper exposure time (normalized to composition 1) | Quality of pattern |
|---|---|---|---|---|
| 1 | NIT | 0.449 g | 1 | + |
| 2 | T2 | 0.589 g | 0.36 | ++ |
| 3 | T35 | 0.574 g | 0.74 | ++ |
| 4 | T3 | 0.784 g | 0.43 | o |

Preparation of Patterned Structures

Compositions 1-4 were used to prepare patterned structures by photolithography by following this general procedure. Each composition was coated on a bare glass wafer with sonication cleaning by a spin coater (1000 rpm, 40 s, ACE-200 model). The coating was soft-baked on a hot plate (LK LAB Korea, PDLP-250 Model with a SUS Cover) at 110° C. for 60 s and subsequently exposed at i-line irradiation of ca. 100-280 mJ/cm² with a photomask patterned with various line-and-space (L/S) sizes (5, 6, 7, 8, 9, and 10 μm) using a CoolUV-100 Mask Aligner with i-line (365 nm) LED light source which was manufactured from Jaesung Engineering Co. (South Korea) at various exposure times. After 1-2 minutes waiting time, the coating in the area exposed to radiation was removed to generate patterned structures by dipping the wafer into a 2.38 wt % aqueous tetramethylammonium hydroxide (TMAH) solution for 1 min at 23° C. Washing was performed by dipping in deionized water for 20 seconds and dried by gently blowing with nitrogen.

Figure 3:
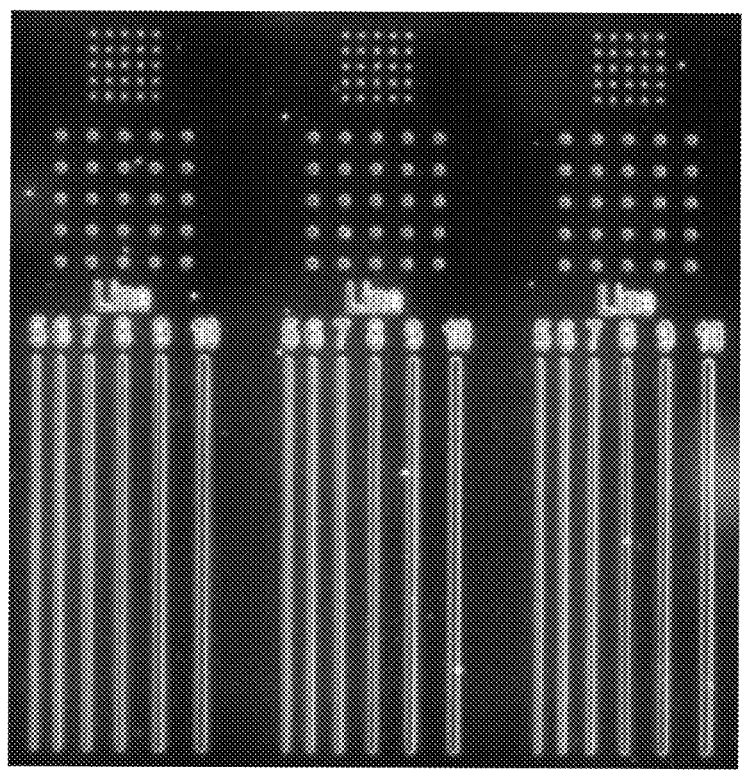
FIG. 3 is a micrograph of patterned structures with various line-and-space (L/S) sizes (5, 6, 7, 8, 9, and 10 um), wherein T2, a compound of the invention, was employed as the PAG compound.

The obtained patterned structures for compositions 1-4 (FIG. 3) were carefully analyzed by a high-resolution microscope. Proper exposure time was determined by stepwise changing the exposure time and checking the pattern after development and drying using a microscope (MU500 model from AmScope Co., magnification: ×500 and minimum 10 um in resolution). Proper exposure was reached, when the pattern showed the same size as the mask. In case of over exposure the width of the space between the lines was wider, and in case of under exposure smaller than the corresponding feature of the mask. Quality of the pattern was determined by checking for lift-off or missing features after development and drying. ++=no lift-off, no missing features, +=no lift off, some small features missing, o=lift-off or all small features missing. Thus, compounds according to the invention uniquely exhibit both high solubility and high sensitivity (short exposure times).

UV-Vis Spectra

Figure 4:
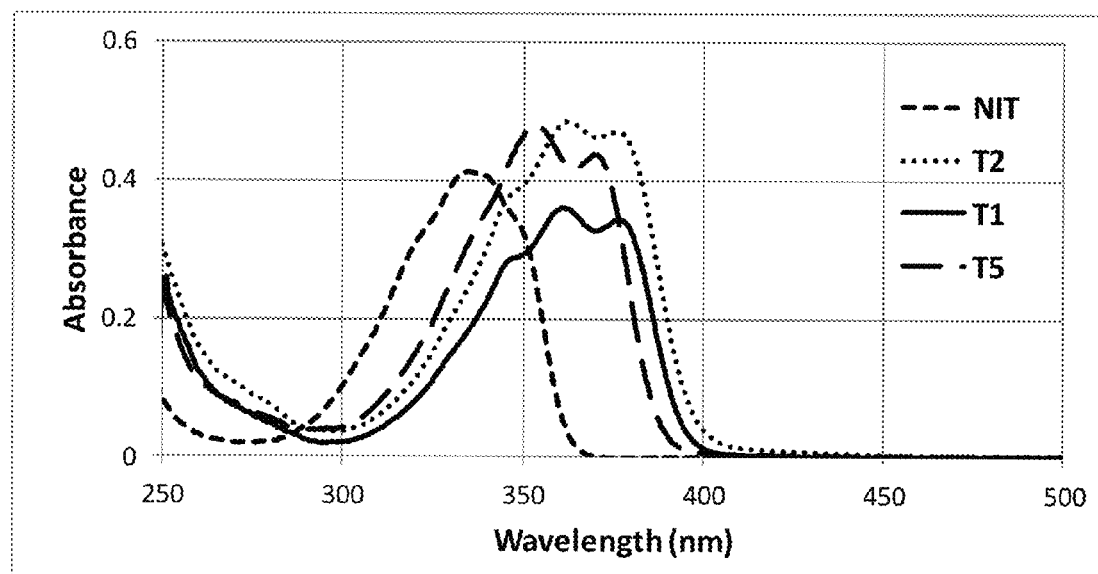
FIG. 4 is a UV-Vis spectra of compounds NIT, T1, T2 and T5 in ACN (0.001% w/v).

As shown in FIG. 4, the PAG compounds of this invention have excellent solubility in organic solvents and strong absorption at i-line of a mercury lamp. Compounds T1 and T2 exhibit an absorption maximum at 362 nm, and compound T5 shows an absorption maximum at 353 nm. Their absorbance at i-line of a mercury lamp is much larger than that of NIT, for example, which is a prior art commercial PAG benchmark for performance. Hence, compounds of the invention exhibit higher sensitivity and better performance as PAGs in photolithography relative to the prior art.

Preparation of PAG Compounds

Examples 2, 3, 4, 5, 6, 7, 8, and 9 describe examples of synthesis of the sulfonic acid derivatives according to this invention.

Example 1: Synthesis of Comparative Compound B

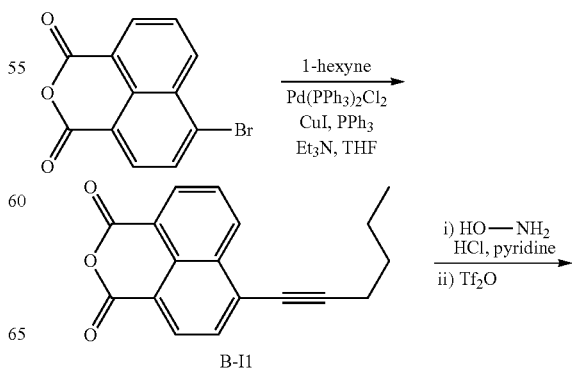

B-I1

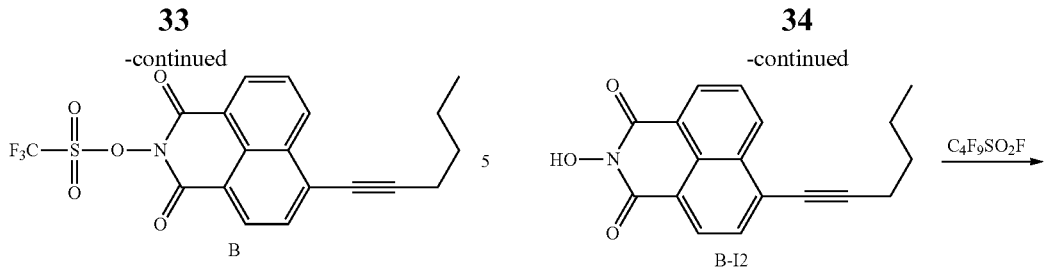

To a 5-L flask was charged 4-bromo-1,8-naphthalic anhydride (263 g, 0.9492 mol), PPh₃ (19.92 g, 75.94 mmol), Et₃N (201.7 g, 1.99 mol) and 2 L of THF. The mixture was stirred under nitrogen for 1 h. To this mixture was added CuI (5.42 g, 28.5 mmol) and Pd(PPh₃)₂Cl₂ (6.66 g, 9.492 mmol) under nitrogen. The mixture was heated to reflux, and 1-hexyne (101.8 g, 1.0 mol) in 0.5 L of THF was added dropwise in 2.5 h. After the addition, the mixture was kept at reflux for 14.5 h. TLC monitoring of the reaction showed a small amount of the unreacted anhydride. An additional amount of 1-hexyne (14.5 g, 142 mmol) was added in 0.5 h, and the mixture was kept at reflux for an additional 2 h. The mixture was allowed to slowly cool down to rt. 20 mL of DI water was added. Filtration gave a yellow solid, and the complete removal of solvents from the filtrate gave a dark brown solid. Both solids were combined and then dissolved in 1 L of CH₂Cl₂. The solution was washed with 1.5 L of DI water. Separation and rotavap of the CH₂Cl₂ solution gave 208 g of the crude solid. Recrystallization from 320 mL of ACN gave 200 g (yield: 70%) of B-I1 as light yellow crystals. Note that B-I1 was used in the subsequent reaction without further purification. Mp: 153-4° C. ¹H NMR (300 MHz, CDCl₃) δ: 8.50 (d, 2H), 8.25 (d, 1H), 7.65 (t, 1H), 7.58 (d, 1H), 2.53 (t, 2H), 1.62 (p, 2H), 1.45 (sextet, 2H), 0.91 (t, 3H). ¹³C NMR (75.5 MHz, CDCl₃) δ: 13.6, 19.6, 22.2, 30.5, 103.5, 117.0, 118.8, 127.5, 129.8, 130.2, 130.6, 131.7, 132.4, 133.4, 133.8, 160.0, 160.4.

To a 1 L flask was charged B-I1 (100 g, 0.3593 mol), H2NOH.HCl (25.49 g, 0.3593 mol), and pyridine (369.49 g, 4.671 mol). The mixture was heated to reflux for 4 h. TLC monitoring the reaction showed the disappearance of B-I1. The reaction mixture was cooled to −13° C. using an ice-salt bath. To this mixture was added dropwise triflic anhydride (222.85 g, 0.7905 mol), and the temperature was kept below 10° C. during the addition. The addition was completed in 4 h. 2 L of DI water was added, and the resulting mixture stirred at room temperature for 1 h. Filtration gave 139 g of the yellow solid. Recrystallization from 100 mL of ACN and 1.2 L of MeOH gave 115 g (yield: 75%) of compound B as light yellow powder. Mp: 112-4° C. 1H NMR (300 MHz, CDCl3) δ: 8.60 (d, 1H), 8.55 (d, 1H), 8.42 (d, 1H), 7.72 (m, 2H), 2.55 (t, 2H), 1.65 (p, 2H), 1.45 (sextet, 2H), 0.95 (t, 3H). 13C NMR (75.5 MHz, CDCl3) δ: 13.6, 19.7, 22.2, 30.5, 77.5, 103.6, 120.0, 121.7, 127.4, 127.6, 130.9, 131.0, 132.1, 132.2, 133.1, 134.5, 158.7, 159.0.

Example 2: Synthesis of Compound T1

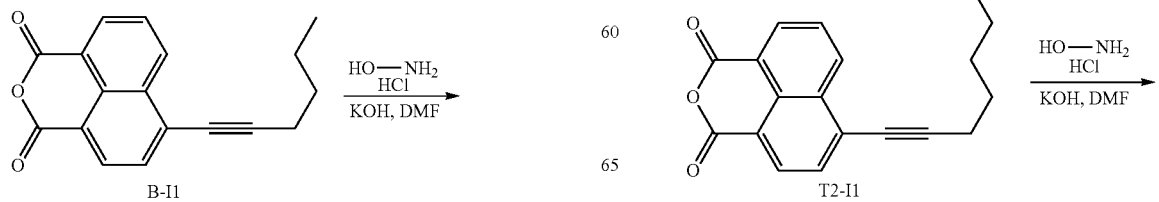

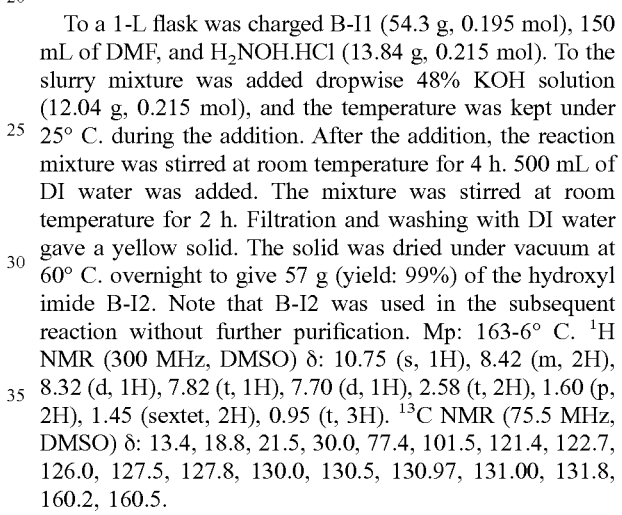

To a 1-L flask was charged B-I1 (54.3 g, 0.195 mol), 150 mL of DMF, and H₂NOH.HCl (13.84 g, 0.215 mol). To the slurry mixture was added dropwise 48% KOH solution (12.04 g, 0.215 mol), and the temperature was kept under 25° C. during the addition. After the addition, the reaction mixture was stirred at room temperature for 4 h. 500 mL of DI water was added. The mixture was stirred at room temperature for 2 h. Filtration and washing with DI water gave a yellow solid. The solid was dried under vacuum at 60° C. overnight to give 57 g (yield: 99%) of the hydroxyl imide B-I2. Note that B-I2 was used in the subsequent reaction without further purification. Mp: 163-6° C. ¹H NMR (300 MHz, DMSO) δ: 10.75 (s, 1H), 8.42 (m, 2H), 8.32 (d, 1H), 7.82 (t, 1H), 7.70 (d, 1H), 2.58 (t, 2H), 1.60 (p, 2H), 1.45 (sextet, 2H), 0.95 (t, 3H). ¹³C NMR (75.5 MHz, DMSO) δ: 13.4, 18.8, 21.5, 30.0, 77.4, 101.5, 121.4, 122.7, 126.0, 127.5, 127.8, 130.0, 130.5, 130.97, 131.00, 131.8, 160.2, 160.5.

The nonaflate T1 was synthesized in 30% yield by the reaction of the hydroxyl imide B-I2 and C₄F₉SO₂F. Mp: 125-8° C. ¹H NMR (300 MHz, CDCl₃) δ: 8.55 (d, 1H), 8.50 (d, 1H), 8.45 (d, 1H), 7.73 (m, 2H), 2.55 (t, 2H), 1.65 (p, 2H), 1.45 (sextet, 2H), 0.95 (t, 3H).

Example 3: Synthesis of Compound T2

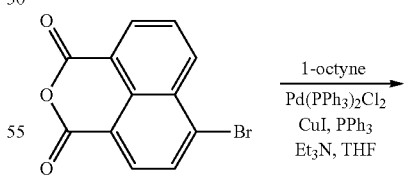

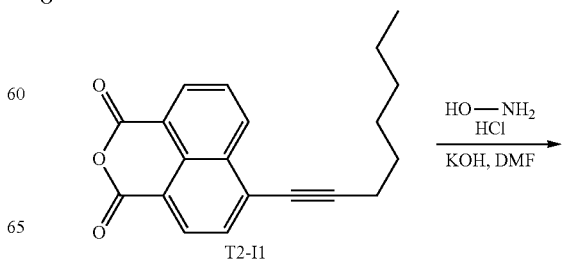

35

-continued

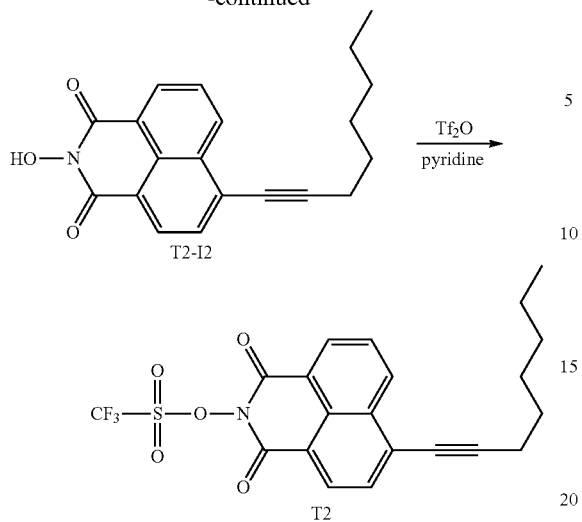

The anhydride intermediate T2-I1 was similarly synthesized in 68% yield by following the same procedure as B-I1 with 1-octyne replacing 1-hexyne. Note that T2-I1 was used in the subsequent reaction without further purification. Mp: 100-1° C. $^1$H NMR (300 MHz, CDCl$_3$) δ: 8.65 (d, 1H), 8.60 (d, 1H), 8.45 (d, 1H), 7.78 (m, 2H), 2.54 (t, 2H), 1.66 (p, 2H), 1.46 (p, 2H), 1.29 (m, 4H), 0.85 (t, 3H).

To a 1-L flask was charged T2-I1 (36 g, 0.1626 mol), 75 mL of DMF, and H$_2$NOH.HCl (13.58 g, 0.1952 mol). To the slurry mixture was added dropwise 48% KOH solution (10.95 g, 0.1952 mol), and the temperature was kept under 25° C. during the addition. After the addition, the reaction mixture was stirred at room temperature for 4 h. 250 mL of DI water was added. The mixture was stirred at room temperature for 2 h. Filtration and washing with DI water gave the yellow solid. The solid was dried under vacuum at 60° C. overnight to give 35 g (yield: 93%) of the hydroxyl imide T2-I2. Note that T2-I2 was used in the subsequent reaction without further purification. Mp: 142-6° C. $^1$H NMR (300 MHz, CDCl$_3$) δ: 8.80 (br s, 1H), 8.54 (m, 2H), 8.42 (d, 1H), 7.70 (m, 2H), 2.54 (t, 2H), 1.67 (p, 2H), 1.48 (p, 2H), 1.29 (m, 4H), 0.85 (t, 3H).

To a 500 mL flask was charged T2-I2 (25 g, 77.8 mmol), acetonitrile (100 mL) and pyridine (9.23 g, 116.7 mmol). The mixture was cooled to 0° C., and triflic anhydride (27.4 g, 197.2 mmol) was then added dropwise below 5° C. during the addition. After the addition, the reaction mixture was allowed to warm to room temperature and stirred at room temperature for 5 h. 300 mL of DI water was added to the mixture. Filtration gave a yellow solid. The solid was dissolved in 100 g of CH$_2$Cl$_2$, and the solution was passed through a short pad of silica gel. Removal of CH$_2$Cl$_2$ and recrystallization from a mixture of isopropanol (200 g) and acetonitrile (20 g) gave a yellow solid which was dried under vacuum at 50° C. overnight to afford 15.9 g (yield: 45%) of T2. Mp: 66-8° C. $^1$H NMR (300 MHz, CDCl$_3$) δ: 8.60 (m, 2H), 8.44 (d, 1H), 7.74 (t, 1H), 2.55 (d, 2H), 1.67 (p, 2H), 1.48 (p, 2H), 1.28 (m, 4H), 0.83 (t, 3H). $^{13}$C NMR (75.5 MHz, CDCl$_3$) δ: 14.0, 20.0, 22.6, 28.4, 28.7, 31.3, 77.5, 103.7, 120.0, 121.7, 127.3, 127.5, 130.8, 130.9, 132.1, 132.2, 133.1, 134.5, 158.7, 159.0.

Example 4: Synthesis of Compound T3

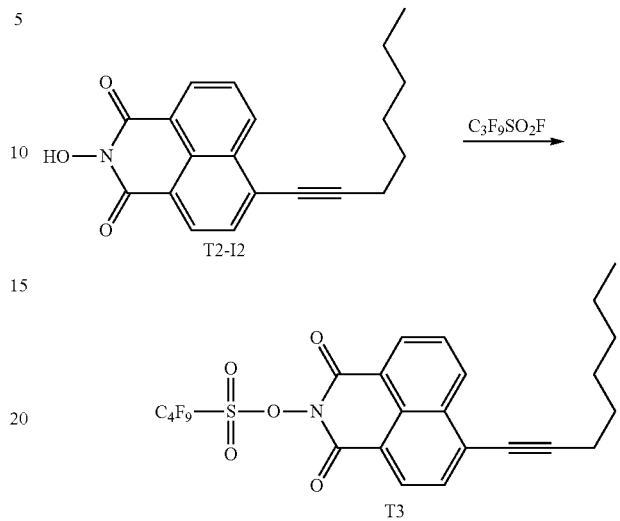

The nonaflate T3 was synthesized in 42% yield by the reaction of the hydroxyl imide T2-I2 and C$_4$F$_9$SO$_2$F. Mp: 115-6° C. $^1$H NMR (300 MHz, CDCl$_3$) δ: 8.60 (m, 2H), 8.42 (d, 1H), 7.74 (m, 2H), 2.52 (t, 2H), 1.65 (p, 2H), 1.45 (m, 2H), 1.28 (m, 2H), 0.95 (t, 3H). $^{13}$C NMR (75.5 MHz, CDCl$_3$) δ: 14.0, 20.0, 22.5, 28.4, 28.7, 31.3, 77.5, 103.6, 120.0, 121.7, 127.3, 127.5, 130.8, 130.9, 132.0, 132.2, 133.1, 134.4, 158.7, 158.9.

Example 5: Synthesis of Compound T5

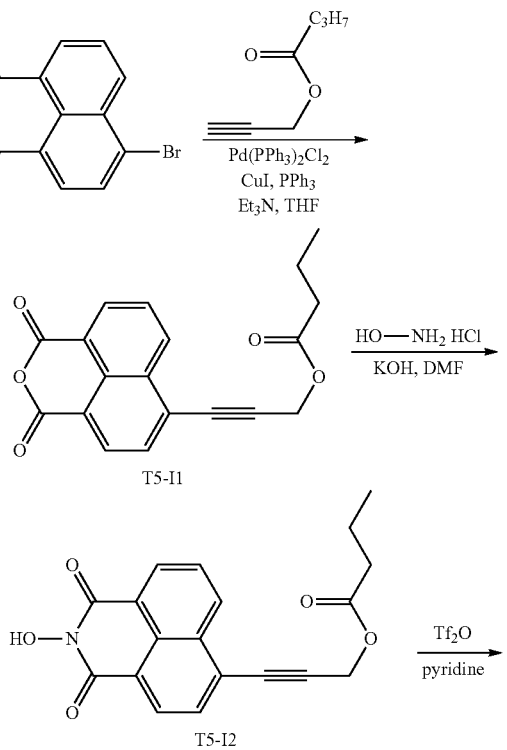

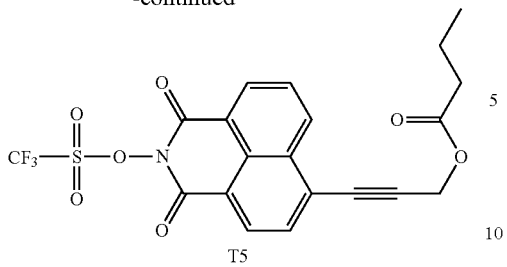

The anhydride intermediate T5-I1 was similarly synthesized in 28% yield by following the same procedure as B-I1 with propargyl butyrate (easily prepared by the reaction of propargyl alcohol with butyryl chloride in the presence of triethylamine) replacing 1-hexyne. Note that T5-I1 was used in the subsequent reaction without further purification. Mp: 135-7° C. $^1$H NMR (300 MHz, CDCl$_3$) δ: 8.63 (m, 2H), 8.49 (d, 1H), 7.84 (m, 2H), 5.02 (s, 2H), 2.36 (t, 2H), 1.67 (sextet, 2H), 0.94 (t, 3H).

To a flask was charged T5-I1 (4.9 g, 15.2 mmol), 10 mL of DMF, and H$_2$NOH.HCl (1.078 g, 16.72 mmol). To the slurry mixture was added dropwise 48% KOH solution (0.938 g, 16.72 mmol), and the temperature was kept under 25° C. during the addition. After the addition, the reaction mixture was stirred at room temperature overnight. 30 mL of DI water was added, and the mixture was stirred at room temperature for 1 h. Filtration and washing with DI water gave the yellow solid. The solid was recrystallized from a mixture of CH$_2$Cl$_2$ and EA to afford 3.5 g (yield: 68%) of the hydroxyl imide, T5-I2. Mp: 180-2° C. $^1$H NMR (300 MHz, CDCl$_3$) δ: 8.60 (m, 2H), 8.50 (d, 1H), 7.82 (m, 2H), 5.02 (s, 2H), 2.36 (t, 2H), 1.67 (sextet, 2H), 0.94 (t, 3H).

To a flask was charged T5-I2 (3.0 g, 8.89 mmol), acetonitrile (15 mL) and pyridine (1.06 g, 13.34 mmol). The mixture was cooled to 0° C., and triflic anhydride (3.13 g, 11.11 mmol) was then added dropwise below 5° C. during the addition. After the addition, the reaction mixture was allowed to warm to room temperature and stirred for 2 h. 100 mL of DI water was added to the mixture. Filtration gave the yellow solid. The solid was dissolved in 10 g of CH$_2$Cl$_2$, and the solution was passed through a short pad of silica gel. Removal of CH$_2$Cl$_2$ and recrystallization from a mixture of isopropanol (20 g) and DI water (2 g) gave a yellow solid which was dried under vacuum at 50° C. to afford 3.2 g (yield: 76%) of T5. Mp: 87-9° C. $^1$H NMR (300 MHz, CDCl$_3$) δ: 8.61 (m, 2H), 8.50 (d, 1H), 7.83 (m, 2H), 5.01 (s, 2H), 2.36 (t, 2H), 1.67 (sextet, 2H), 0.93 (t, 3H). $^{13}$C NMR (75.5 MHz, CDCl$_3$) δ: 13.6, 18.4, 35.9, 52.2, 82.3, 94.7, 120.8, 121.3, 121.8, 127.2, 128.1, 131.5, 131.8, 132.1, 133.3, 134.2, 158.5, 158.8, 172.9.

Example 6: Synthesis of Compound T35

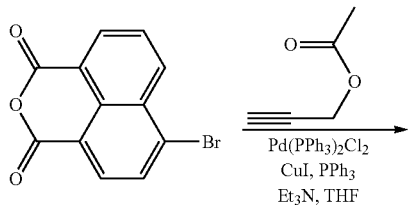

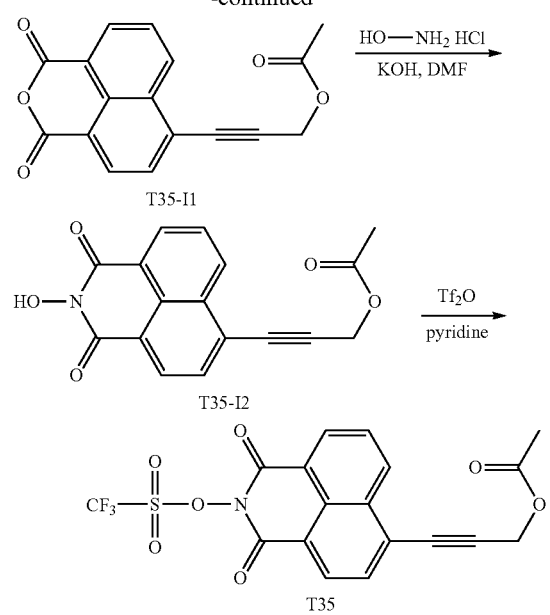

The anhydride intermediate T35-I1 was similarly synthesized in 64% yield by following the same procedure as B-I1 with propargyl butyrate (easily prepared by the reaction of propargyl alcohol with acetyl chloride in the presence of triethylamine) replacing 1-hexyne. Note that T35-I1 was used in the subsequent reaction without further purification. Mp: 173-6° C. $^1$H NMR (300 MHz, CDCl$_3$) δ: 8.60 (m, 2H), 8.46 (d, 1H), 7.82 (m, 2H), 5.01 (s, 2H), 2.13 (s, 3H).

To a flask was charged T35-I1 (10 g, 34.0 mmol), 15 mL of DMF, and H$_2$NOH.HCl (2.60 g, 37.4 mmol). To the slurry mixture was added dropwise 48% KOH solution (2.10 g, 37.4 mmol), and the temperature was kept under 25° C. during the addition. After the addition, the reaction mixture was stirred at room temperature overnight. 30 mL of DI water was added. The mixture was stirred at room temperature for 1 h. Filtration and washing with DI water gave the solid which was dried under vacuum at 60° C. to afford 9.0 g (yield: 86%) of the hydroxyl imide, T35-I2. Note that T35-I1 was used in the subsequent reaction without further purification.

To a flask was charged T35-I2 (8.7 g, 28.1 mmol), acetonitrile (50 mL) and pyridine (3.33 g, 42.1 mmol). The mixture was cooled to 0° C., and triflic anhydride (9.9 g, 35.1 mmol) was then added dropwise below 5° C. during the addition. After the addition, the reaction mixture was allowed to warm to room temperature and stirred at room temperature for 2 h. 100 mL of DI water was added to the mixture. Filtration gave the yellow solid. The solid was dissolved in 10 g of CH$_2$Cl$_2$, and the solution was passed through a short pad of silica gel. Removal of CH$_2$Cl$_2$ and recrystallization from a mixture of isopropanol (50 mL) and ACN (25 mL) gave a yellow solid which was dried under vacuum at 50° C. overnight to afford 8 g (yield: 64%) of T35. Mp: 157-9° C. $^1$H NMR (300 MHz, CDCl$_3$) δ: 8.61 (m, 2H), 8.50 (d, 1H), 7.83 (m, 2H), 5.01 (s, 2H), 2.13 (s, 3H). $^{13}$C NMR (75.5 MHz, CDCl$_3$) δ: 20.7, 52.4, 82.4, 94.4, 121.4, 121.8, 127.3, 128.1, 128.5, 131.6, 131.8, 132.1, 133.4, 134.2, 158.5, 158.8, 172.9.

Example 7: Synthesis of Compound T38

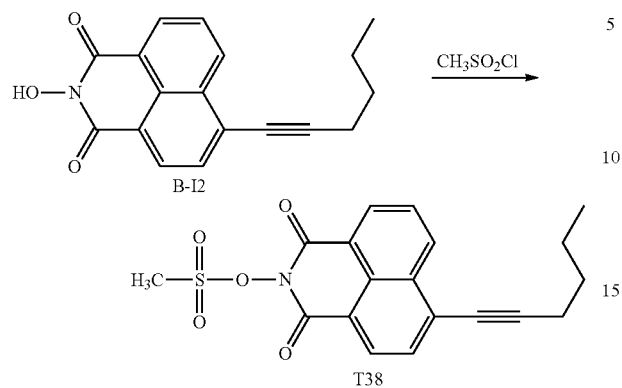

To a 1-L flask was charged B-I2 (15 g, 51.1 mmol), 60 mL of ACN, and Et₃N (5.7 g, 56.2 mmol). The mixture was cooled to 0° C., and CH₃SO₂Cl (6.44 g, 56.2 mmol) was added dropwise. After the addition, the reaction mixture was allowed to warm to room temperature and stirred at room temperature for 3 h. 200 mL of DI water was added, and the mixture was stirred at room temperature for 1 h. Filtration and washing with DI water gave 18.6 of the yellow solid. The solid was recrystallized from EA to give 16.7 g (yield: 88%) of T38. Mp: 121-2° C. $^1$H NMR (300 MHz, CDCl₃) δ: 8.60 (m, 2H), 8.45 (d, 1H), 7.72 (m, 2H), 3.52 (s, 3H), 2.55 (t, 2H), 1.62 (p, 2H), 1.50 (m, 2H), 0.95 (t, 3H).

Example 8: Synthesis of Compound T40

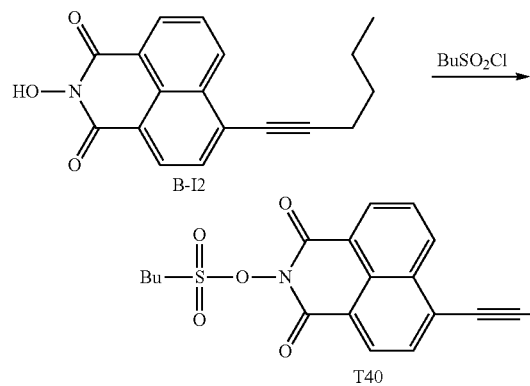

To a 1-L flask was charged B-I2 (20 g, 68.2 mmol), 80 mL of ACN, and Et₃N (7.6 g, 75 mmol). The mixture was cooled to 0° C., and BuSO₂Cl (11.74 g, 75 mmol) was added dropwise. After the addition, the reaction mixture was allowed to warm to room temperature and stirred at room temperature for 3 h. 200 mL of DI water was added, and the mixture was stirred at room temperature for 1 h. Filtration and washing with DI water gave the yellow solid. The solid was recrystallized from ACN to give 25.6 g (yield: 91%) of T40. Mp: 110-1° C. $^1$H NMR (300 MHz, CDCl₃) δ: 8.45 (m, 2H), 8.35 (d, 1H), 7.62 (m, 2H), 3.62 (t, 2H), 2.52 (t, 2H), 2.02 (m, 2H), 1.62 (m, 2H), 1.45 (m, 4H), 0.95 (m, 6H).

Example 9: Synthesis of Compound T39

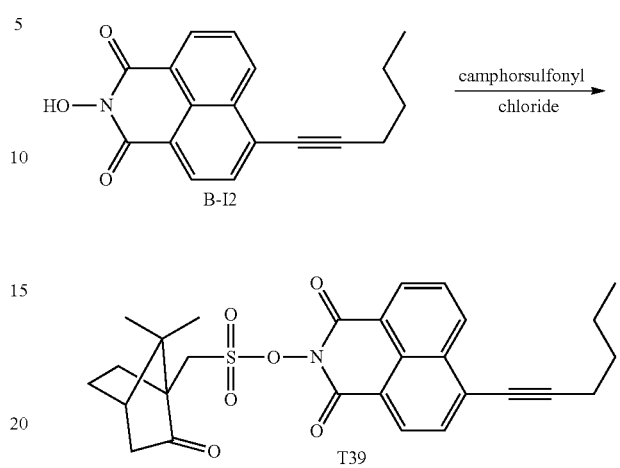

To a 1-L flask was charged B-I2 (15 g, 51.1 mmol), 80 mL of ACN, and Et₃N (5.7 g, 56.2 mmol). The mixture was cooled to 0° C., and camphorsulfonyl chloride (14.1 g, 56.2 mmol) was added dropwise. After the addition, the reaction mixture was allowed to warm to room temperature and stirred at room temperature for 3 h. 200 mL of DI water was added, and the mixture was stirred at room temperature for 1 h. Filtration and washing with DI water gave the yellow solid. The solid was recrystallized from EA to give 18 g (yield: 70%) of T39. Mp: 124-6° C. $^1$H NMR (300 MHz, CDCl₃) δ: 8.60 (m, 2H), 8.50 (d, 1H), 7.65 (m, 2H), 4.15 (d, 1H), 3.85 (d, 1H), 2.55 (t, 2H), 2.40 (m, 2H), 1.30-2.10 (br m, 9H), 1.12 (s, 3H), 0.95 (m, 6H).

Example 10: Synthesis of Comparative Compound A

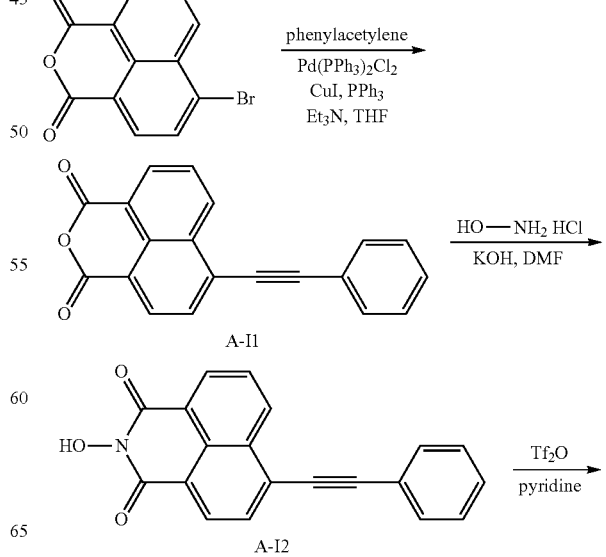

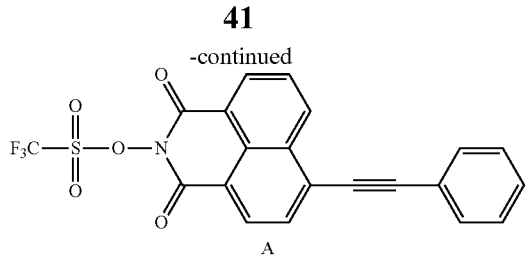

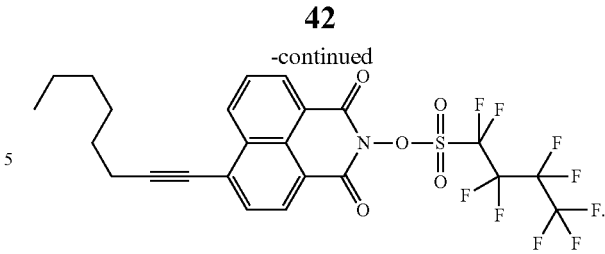

The anhydride intermediate A-I1 was similarly synthesized in 75% yield by following the same procedure as B-I1 with phenylacetylene replacing 1-hexyne. Note that A-I1 was used in the subsequent reaction without further purification.

To a 1-L flask was charged A-I1 (81 g, 271.5 mmol), 250 mL of DMF, and H$_2$NOH.HCl (18.4 g, 285.1 mmol). To the slurry mixture was added dropwise 48% KOH solution (16.0 g, 285.1 mmol), and the temperature was kept under 25° C. during the addition. After the addition, the reaction mixture was stirred at room temperature for 4 h. 250 mL of DI water was added. The mixture was stirred at room temperature for 2 h. Filtration and washing with DI water gave the yellow solid. The solid was dried under vacuum at 60° C. overnight to give 80 g (yield: 94%) of the hydroxyl imide A-I2. Note that A-I2 was used in the subsequent reaction without further purification. Mp: 194-9° C.

To a 500 mL flask was charged A-I2 (55 g, 175.5 mmol), acetonitrile (200 mL) and pyridine (23.6 g, 298.4 mmol). The mixture was cooled to 0° C., and triflic anhydride (74.3 g, 263.3 mmol) was then added dropwise below 5° C. during the addition. After the addition, the reaction mixture was allowed to warm to room temperature and stirred at room temperature overnight. The mixture was heated to reflux for 30 min and cooled down to rt. 200 mL of DI water was added to the mixture and stirred at room temperature for 10 min. Filtration gave the yellow solid which was dissolved in 1 L of CH$_2$Cl$_2$, and the solution was passed through a short pad of silica gel. The solution was subject to rotavap until 100 g of CH$_2$Cl$_2$ was left. Filtration gave a yellow solid which was dried under vacuum at 50° C. overnight to afford 46 g (yield: 59%) of A. Mp: 193-5° C. $^1$H NMR (300 MHz, DMSO) δ: 8.94 (d, 1H), 8.70 (d, 1H), 8.63 (d, 1H), 8.18 (d, 1H), 8.10 (dd, 1H) 7.82 (m, 2H), 7.52 (m, 3H).

Although illustrated and described above with reference to certain specific embodiments and examples, the invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. A sulfonic acid derivative compound selected from the group consisting of

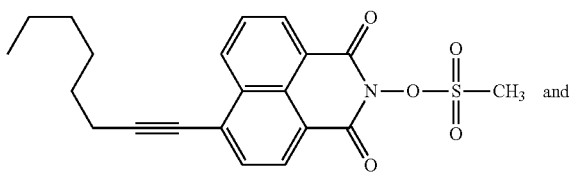

2. A photoresist composition comprising:
   (i) at least one sulfonic acid derivative compound of the following formulas:

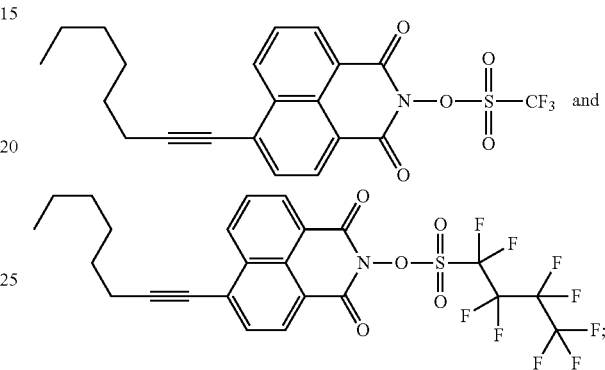

(ii) at least one polymer or copolymer which is capable of being imparted with an altered solubility in an aqueous solution in the presence of an acid;
   (iii) an organic solvent; and, optionally,
   (iv) an additive.

3. The composition according to claim 2, wherein the organic solvent is propylene glycol monomethyl ether acetate (PGMEA).

4. The composition according to claim 3 comprising:
   0.05 to 15 wt. % of the sulfonic acid derivative compound;
   5 to 50 wt. % of the at least one polymer or copolymer;
   0 to 10 wt. % of the additive; and
   reminder is propylene glycol monomethyl ether acetate.

5. A process of producing a patterned structure on the surface of a substrate, the process comprising the steps of
   (a) applying a layer of the composition according to claim 4 onto the surface of the substrate and at least partial removal of the organic solvent (iv);
   (b) exposing the layer to electromagnetic radiation, thereby releasing an acid from the sulfonic acid derivative compound (i) in the areas exposed to the electromagnetic radiation;
   (c) optionally heating the layer to impart compound (ii) in the areas in which the acid has been released with an increased solubility in an aqueous solution; and
   (d) at least partial removal of the layer with an aqueous solution in these areas.

6. The process of claim 5 wherein, during the exposing step, the sulfonic acid derivative compound exhibits a photoreactivity of from 8 to 10 times greater relative to N-hydroxynaphthalimide triflate (NIT) in an otherwise identical composition.

7. The process of claim 5 wherein the applying step is accomplished by a method selected from the group consisting of spin coating, spray coating, dip coating, and doctor blading.

8. The process of claim 5 wherein the substrate is selected from the group consisting of silicon, silicon dioxide, silicon-on-insulator (SOI), strained silicon, gallium arsenide, and coated substrates, wherein the coating is selected from the group consisting of silicon nitride, silicon oxynitride, titanium nitride, tantalum nitride, hafnium oxide, titanium, tantalum, copper, aluminum, tungsten, alloys thereof, and combinations thereof.

9. The composition of claim 2, wherein the additive is a basic quencher.

10. The composition of claim 9, wherein the basic quencher is selected from the group consisting of N,N-bis(2-hydroxyethyl)pivalamide, N,N-Diethylacetamide, N1,N1,N3,N3-tetrabutylmalonamide, 1-methylazepan-2-one, 1-allylazepan-2-one and tert-butyl 1,3-dihydroxy-2-(hydroxymethyl)propan-2-ylcarbamate, pyridine, di-tert-butyl pyridine, triisopropanolamine, n-tert-butyldiethanolamine, tris(2-acetoxy-ethyl)amine, 2,2',2'',2'''-(ethane-1,2-diylbis(azanetriyl))tetraethanol, 2-(dibutylamino)ethanol, 2,2',2''-nitrilotriethanol, 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate, and N(2-acetoxy-ethyl)morpholine.

11. The composition of claim 10, wherein the basic quencher is selected from the group consisting of 1-(tert-butoxycarbonyl)-4-hydroxypiperidine and triisopropanolamine.

12. A photoresist composition comprising:
(i) a sulfonic acid derivative compound according to the following formula:

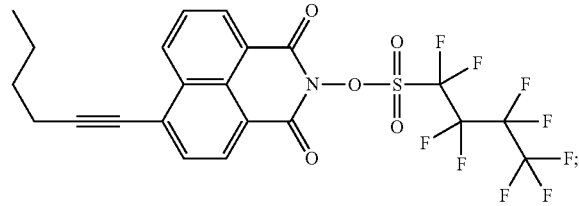

(ii) at least one polymer or copolymer which is capable of being imparted with an altered solubility in an aqueous solution in the presence of an acid;
(iii) an organic solvent; and, optionally,
(iv) an additive.

13. The composition according to claim 12, wherein the organic solvent is propylene glycol monomethyl ether acetate (PGMEA).

14. The composition according to claim 13 comprising:
0.05 to 15 wt. % of the sulfonic acid derivative compound;
5 to 50 wt. % of the at least one polymer or copolymer;
0 to 10 wt. % of the additive; and
reminder is propylene glycol monomethyl ether acetate.

15. A process of producing a patterned structure on the surface of a substrate, the process comprising the steps of
(a) applying a layer of the composition according to claim 14 onto the surface of the substrate and at least partial removal of the organic solvent (iv);
(b) exposing the layer to electromagnetic radiation, thereby releasing an acid from the sulfonic acid derivative compound (i) in the areas exposed to the electromagnetic radiation;
(c) optionally heating the layer to impart compound (ii) in the areas in which the acid has been released with an increased solubility in an aqueous solution; and
(d) at least partial removal of the layer with an aqueous solution in these areas.

16. The process of claim 15 wherein, during the exposure step, the sulfonic acid derivative compound exhibits a photoreactivity of from 8 to 10 times greater relative to N-hydroxynaphthalimide triflate (NIT) in an otherwise identical composition.

17. The composition of claim 15, wherein the additive is a basic quencher.

18. The composition of claim 17, wherein the basic quencher is selected from the group consisting of N,N-bis(2-hydroxyethyl)pivalamide, N,N-Diethylacetamide, N1,N1,N3,N3-tetrabutylmalonamide, 1-methylazepan-2-one, 1-allylazepan-2-one and tert-butyl 1,3-dihydroxy-2-(hydroxymethyl)propan-2-ylcarbamate, pyridine, di-tert-butyl pyridine, triisopropanolamine, n-tert-butyldiethanolamine, tris(2-acetoxy-ethyl)amine, 2,2',2'',2'''-(ethane-1,2-diylbis(azanetriyl))tetraethanol, 2-(dibutylamino)ethanol, 2,2',2''-nitrilotriethanol, 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate, and N(2-acetoxy-ethyl)morpholine.

19. The composition of claim 18, wherein the basic quencher is selected from the group consisting of 1-(tert-butoxycarbonyl)-4-hydroxypiperidine and triisopropanolamine.

20. The process of claim 15 wherein the applying step is accomplished by a method selected from the group consisting of spin coating, spray coating, dip coating, and doctor blading.

21. The process of claim 15 wherein the substrate is selected from the group consisting of silicon, silicon dioxide, silicon-on-insulator (SOI), strained silicon, gallium arsenide, and coated substrates, wherein the coating is selected from the group consisting of silicon nitride, silicon oxynitride, titanium nitride, tantalum nitride, hafnium oxide, titanium, tantalum, copper, aluminum, tungsten, alloys thereof, and combinations thereof.

* * * * *